United States Patent
Belgrader

(10) Patent No.: US 12,258,619 B2
(45) Date of Patent: *Mar. 25, 2025

(54) SAMPLE SPLITTING FOR MULTIPLEXED DETECTION OF NUCLEIC ACIDS WITHOUT AMPLIFICATION

(71) Applicant: VedaBio, Inc., San Diego, CA (US)

(72) Inventor: Phillip Belgrader, San Diego, CA (US)

(73) Assignee: VedaBio, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/765,750

(22) Filed: Jul. 8, 2024

(65) Prior Publication Data

US 2025/0002977 A1   Jan. 2, 2025

Related U.S. Application Data

(63) Continuation of application No. 18/406,159, filed on Jan. 7, 2024, now Pat. No. 12,060,602.

(60) Provisional application No. 63/438,147, filed on Jan. 10, 2023.

(51) Int. Cl.
| | |
|---|---|
| C12Q 1/6823 | (2018.01) |
| C12N 9/22 | (2006.01) |
| C12N 15/11 | (2006.01) |
| C12Q 1/44 | (2006.01) |
| C12Q 1/6806 | (2018.01) |
| G01N 21/64 | (2006.01) |

(52) U.S. Cl.
CPC ............ *C12Q 1/6823* (2013.01); *C12N 9/22* (2013.01); *C12N 15/111* (2013.01); *C12Q 1/44* (2013.01); *C12Q 1/6806* (2013.01); *G01N 21/6486* (2013.01); *C12N 2310/20* (2017.05)

(58) Field of Classification Search
None
See application file for complete search history.

(56) References Cited

U.S. PATENT DOCUMENTS

| | | |
|---|---|---|
| 10,253,365 B1 | 4/2019 | Doudna et al. |
| 10,266,886 B2 | 4/2019 | Abudayyeh et al. |
| 10,266,887 B2 | 4/2019 | Abudayyeh et al. |
| 10,337,051 B2 | 7/2019 | Doudna et al. |
| 10,377,998 B2 | 8/2019 | Zhang et al. |
| 10,494,664 B2 | 12/2019 | Doudna et al. |
| 10,533,152 B1 | 1/2020 | Belgrader et al. |
| 11,021,740 B2 | 6/2021 | Abudayyeh et al. |
| 11,060,115 B2 | 7/2021 | Severinov et al. |
| 11,104,937 B2 | 8/2021 | Abudayyeh et al. |
| 11,118,224 B2 | 9/2021 | Doudna et al. |
| 11,149,259 B2 | 10/2021 | Zhang et al. |
| 11,174,470 B2 | 11/2021 | Harrington et al. |
| 11,174,515 B2 | 11/2021 | Abudayyeh et al. |
| 11,273,442 B1 | 3/2022 | Chen et al. |
| 11,421,250 B2 | 8/2022 | Severinov et al. |
| 11,447,824 B2 | 9/2022 | Doudna et al. |
| 11,584,955 B2 | 2/2023 | Wang et al. |
| 2010/0286082 A1 | 11/2010 | Breaker et al. |
| 2014/0377748 A1 | 12/2014 | Tan et al. |
| 2016/0040189 A1 | 2/2016 | Kennedy et al. |
| 2016/0083785 A1 | 3/2016 | Bone et al. |
| 2016/0186213 A1 | 6/2016 | Zhang et al. |
| 2018/0023081 A1 | 1/2018 | Hagedorn et al. |
| 2018/0155716 A1 | 6/2018 | Zhang et al. |
| 2018/0282722 A1 | 10/2018 | Jakimo et al. |
| 2019/0046989 A1 | 2/2019 | Ririe et al. |
| 2019/0112648 A1 | 4/2019 | Schaal et al. |
| 2019/0201550 A1 | 7/2019 | Maeder et al. |
| 2019/0241954 A1 | 8/2019 | Doudna et al. |
| 2019/0256900 A1 | 8/2019 | Zhang et al. |
| 2019/0344269 A1 | 11/2019 | Johnson et al. |
| 2020/0010879 A1 | 1/2020 | Doudna et al. |
| 2020/0056167 A1 | 2/2020 | Dong et al. |
| 2020/0157611 A1 | 5/2020 | Qi et al. |
| 2020/0165594 A1 | 5/2020 | Zhang et al. |
| 2020/0277600 A1 | 9/2020 | Zhang et al. |
| 2020/0392473 A1 | 12/2020 | Zhang et al. |
| 2021/0102183 A1 | 4/2021 | Cameron et al. |
| 2021/0102242 A1 | 4/2021 | Chen et al. |
| 2021/0108267 A1 | 4/2021 | Zhang et al. |
| 2021/0163944 A1 | 6/2021 | Zhang et al. |
| 2021/0166783 A1 | 6/2021 | Shmakov et al. |
| 2021/0269866 A1 | 9/2021 | Zhang et al. |

(Continued)

FOREIGN PATENT DOCUMENTS

| | | |
|---|---|---|
| CN | 113324956 | 8/2021 |
| CN | 114058679 A | 2/2022 |

(Continued)

OTHER PUBLICATIONS

Li, et al., "Applying CRISPR-Cas12a as Signal Amplifier to Construct Biosensors for Non-DNA Targets in Ultra-low Concentrations", ACS Sensors, doi: 10.1021/acssensors.9b02305, pp. 1-23, Mar. 12, 2020.

Kim, et al., "Chimeric crRNAs with 19 DNA residues in the guide region show retained DNA cleavage activity of Cas9 with a potential to improve the specificity", The Royal Society of Chemistry, pp. 1-16, 2019.

Kim, et al., "Enhancement of target specificity of CRISPR-Cas12a by using a chimeric DNA-RNA guide", Nucleic Acids Research, doi: 10.1093/nar/gkaa605, vol. 48, No. 15, pp. 8601-8616, Jul. 20, 2020.

(Continued)

*Primary Examiner* — Sean McGarry
(74) *Attorney, Agent, or Firm* — Sarah Brashears

(57) ABSTRACT

The present disclosure relates to multiplex assay methods used to detect target nucleic acids of interest from several to many sources in a sample without amplification of the target nucleic acids of interest. The methods involve partitioning of first ribonucleoprotein complexes to detect short sequences from several to many loci scattered throughout a single source genome, and the addition of signal boosting second ribonucleoprotein complexes and reporter moieties.

30 Claims, 6 Drawing Sheets

(56) References Cited

U.S. PATENT DOCUMENTS

| | | |
|---|---|---|
| 2021/0317527 A1 | 10/2021 | Doudna et al. |
| 2021/0388437 A1 | 12/2021 | Doudna et al. |
| 2022/0025463 A1 | 1/2022 | Abudayyeh et al. |
| 2022/0333208 A1 | 10/2022 | Gootenberg et al. |
| 2023/0193368 A1 | 6/2023 | Rananaware et al. |

FOREIGN PATENT DOCUMENTS

| | | |
|---|---|---|
| CN | 114262730 A | 4/2022 |
| WO | WO 2014/143228 A1 | 9/2014 |
| WO | WO 2016/201138 A1 | 12/2016 |
| WO | WO 2020/191248 | 9/2020 |
| WO | WO 2020/191376 | 9/2020 |
| WO | WO 2021/021532 A1 | 2/2021 |
| WO | WO 2021/108717 A2 | 6/2021 |
| WO | WO 2021/146534 A1 | 7/2021 |
| WO | WO 2021/236651 A1 | 11/2021 |
| WO | WO 2021/243276 | 12/2021 |
| WO | WO 2022/061166 A1 | 3/2022 |
| WO | WO 2022/133108 A2 | 6/2022 |
| WO | WO 2022/266513 A2 | 12/2022 |
| WO | WO 2023/278629 A1 | 1/2023 |
| WO | WO 2023/287669 A2 | 1/2023 |
| WO | WO 2023/015259 A2 | 2/2023 |
| WO | WO 2023/056451 A1 | 4/2023 |
| WO | WO 2023/081902 A1 | 5/2023 |
| WO | WO 2023/114052 A1 | 6/2023 |
| WO | WO 2023/114090 A2 | 6/2023 |
| WO | WO 2024/2067133 A1 | 10/2024 |

OTHER PUBLICATIONS

Swarts, et al., "Mechanistic Insights into the Cis- and Trans-acting Deoxyribonuclease Activities of Cas12a", Mol Cell, doi: 10.1016/j.molcel.2018.11.021, pp. 1-28, Feb. 7, 2019.

Nguyen, et al., "Enhancement of trans-cleavage activity of Cas12a with engineered crRNA enables amplified nucleic acid detection", Nature Communications, doi: 10.1038/s41467-020-18615-1, pp. 1-13, 2020.

Ooi, et al., "An engineered CRISPR-Cas12a variant and DNA-RNA hybrid guides enable robust and rapid COVID-10 testing", Nature Communications, doi: 10.1038/s41467-021-21996-6, pp. 1-23, 2021.

Shi, et al., "A CRISPR-Cas autocatalysis-driven feedback amplification network for supersensitive DNA diagnostics", Science Advances, doi: 10.1126/sciadv.abc7802, pp. 1-9, Jan. 27, 2021.

The Board of Trustees of the University of Illinois, "CRISPR Cascade", International PCT Application No. PCT/US22/33985, filed Jun. 17, 2022.

Chen, et al., "CRISPR-Cas12a target binding unleashes indiscriminate single-stranded DNase activity", Howard Hughes Medical Institute, Science, 360(6387), pp. 436-439, Apr. 27, 2018.

Liu, et al., "Accelerated RNA detection using tandem CRISPR nucleases", Nature Chemical Biology, vol. 17, doi:10.1038/s41589-021-0084202, pp. 982-988, Sep. 2021.

Gootenberg, et al., "Nucleic acid detection with CRISPR-Cas13a/C2c2", Science, doi:10.1126/science.aam9321, pp. 438-442, Apr. 28, 2017.

Fozouni, et al., "Amplification-free detection of SARS-CoV-2 with CRISPR-Cas13a and mobile phone microscopy", Cell, doi.org/10.1016/j.cell.2020.12.001, pp. 323-333, Jan. 21, 2021.

Kaminski, et al., "CRISPR-based diagnostics", Nature Biomedical Engineering, vol. 5, doi.org/10.1038/s41551-021-00760-7, pp. 643-656, Jul. 2021.

Zhou, et al., "CRISPR/Cas13a Powered Portable Electrochemiluminescence Chip for Ultrasensitive and Specific MiRNA Detection", Advanced Science News, doi: 10.1002/advs.201903661, pp. 1-10, 2020.

Zhao, et al., "CRISPR-Cas13a system: A novel tool for molecular diagnostics", Frontiers in Microbiology, doi:10.3389/fmicb.2022.1060947, pp. 1-18, Dec. 8, 2022.

Zhou, et al., "A Decade of CRISPR Gene Editing in China and Beyond: A Scientometric Landscape", The CRISPR Journal, vol. 4, No. 3, doi:10.1089/crispr.2020.0148, pp. 313-320, 2021.

Shinoda, et al., "Automated amplification-free digital RNA detection platform for rapid and sensitive SARS-CoV-2 diagnosis", Communications Biology, doi.org/10.1038/s42003-022-03433-6, pp. 1-8, May 26, 2022.

Gupta, et al., "Cas13d: A New Molecular Scissor for Transcriptome Engineering", Frontiers in Cell and Developmental Biology, vol. 10, doi:10.3389/fcell.2022.866800, pp. 1-22, Mar. 31, 2022.

Schunder, et al., "First indication for a functional CRISPR/Cas system in Francisella tularensis", International Journal of Medical Microbiology, vol. 303, Issue 2, doi:10.1016/j.ijmm.2012.11.004, pp. 1-29, Mar. 2013.

Sha, et al., "Cascade CRISPR/cas enables amplification-free microRNA sensing with fM-sensitivity and single-base-specificity", ChemComm, doi:10.1039/d0cc06412b, pp. 247-250 and 1-15, 2021.

Yang, et al., "Engineered LwaCas13a with enhanced collateral activity for nucleic acid detection", Nature Chemical Biology, vol. 19, doi:10.1038/s41589-022-01135-y, pp. 45-54, Jan. 2023.

East-Seletsky, et al., "RNA targeting by functionally orthogonal Type VI-A CRISPR-Cas enzymes", Howard Hughes Medical Institute, Mol Cell, pp. 373-383, May 4, 2017.

Schmidt, et al., "Application of locked nucleic acids to improve aptamer in vivo stability and targeting function", Nucleic Acids Research, vol. 32, No. 19, doi:10.1093/nar/gkh862, pp. 5757-5765, Oct. 27, 2004.

Makarova, et al., "Evolutionary classification of CRISPR-Cas systems: a burst of class 2 and derived variants", Nature Reviews | Microbiology, vol. 18, pp. 67-83, Feb. 2020.

Gleditzsch, et al., "PAM identification by CRISPR-Cas effector complexes: diversified mechanisms and structures", RNA Biology, vol. 16, No. 4, doi.org/10.1080/15476286.2018.1504546, pp. 504-517, Jul. 20, 2018.

Kellner, et al., "Sherlock: Nucleic acid detection with CRISPR nucleases", Nat Protoc., doi:10.1038/s41596-019-0210-2, pp. 2986-3012, Oct. 2019.

Liu, et al., "Directed Evolution of CRISPR/Cas Systems for Precise Gene Editing", Trends in Biotechnology, vol. 39, No. 3, Mar. 2021, p. 262-273.

International Search Report and Written Opinion for International Application No. PCT/US2022/036610, dated Jun. 29, 2023, p. 1-93.

International Search Report and Written Opinion for International Application No. PCT/US22/52320, dated Jun. 15, 2023, p. 1-46.

International Search Report and Written Opinion for International Application No. PCT/US2022/052032, dated Apr. 18, 2023, p. 1-19.

Zhang, et al, "An aM-level cascade CRISPR-Dx system (ASCas) for rapid detection of RNA without pre-amplification", Biosensors and Bioelectronics, doi:10.1016/j.bios.2023.115248, Mar. 28, 2023, p. 1-5.

Zeng, et al., "Rapid RNA detection through intra-enzyme chain replacement-promoted Cas13a cascade cyclic reaction without amplification", Analytica Chimica Acta, doi:10.1016/j.aca.2022.340009, May 31, 2022, p. 1-10.

Collias, et al., "CRISPR technologies and the search for the PAM-free nuclease", Nature Communications, doi: 10.1038/s41467-020-20633-y, 2021, p. 1-12.

Huyke, et al., "Enzyme Kinetics and Detector Sensitivity Determine Limits of Detection of Amplification-Free CRISPR-Cas12 and CRISPR-Cas13 Diagnostics", Analytical Chemistry, doi:10.1021/acs.analchem.2601670, Jun. 27, 2022, p. 9826-9834.

Mullally, et al., "5' modifications to CRISPR-Cas9 gRNA can change the dynamics and size of R-loops and inhibit DNA cleavage", Nucleic Acids Research, DOI:10.1093/nar/gkaa477, Jun. 2020, vol. 48, No. 12, p. 6811-6823.

Hong, et al., "Comparison and optimization of CRISPR/dCas9/gRNA genome-labeling systems for live cell imaging", Genome Biology, DOI: 10.1186/s13059-018-1413-5, 2018, p. 7-8.

Li, et al., "CRISPR-Cas 12a has both cis- and trans-cleavage activities on single-stranded DNA", Cell Research, DOI: 10.1038/s41422-018-0022-x, Feb. 5, 2018, p. 1-3.

(56) References Cited

OTHER PUBLICATIONS

Dong, et al., "An anti-CRISPR protein disables type V Cas12a by acetylation", PubMed, DOI:10.1038/s41594-019-0206-1, Feb. 28, 2023, p. 1-1.
Coehlo, et al., "CRISPR Guard protects off-target sites from Cas9 nuclease activity using short guide RNAs", Nature Communications, DOI: 10.1038/s41467-020-17952-5, Aug. 17, 2020, p. 1-12.
Click Chemistry, "Introduction: Click Chemistry", Chem. Rev. 2021, doi/10.1021/acs.chemrev.1c00469, p. 6697-6698.
MacConnell, et al., "An Integrated Microfluidic Processor for DNA-Encoded Combinatorial Library Functional Screening", ACS Combinatorial Science, DOI: 10.1021/acscombsci.6b00192, p. 181-192.
Mendes, et al., "High-throughput Identification of DNA-Encoded IgG Ligands that Distinquish Active and Latent *Mycobacterium tuberculosis* Infections", ACS Chem Biol., Jan. 20, 2017, doi:10.1021/acschembio.6b00855, p. 1-19.
Gerry, et al., "Unifying principles of bifunctional, proximity-inducing small molecules", Nat Chem Biol., Apr. 1, 2020, doi:10.1038/s41589-020-0469-1, p. 1-24.
Bowley, et al., "Libraries against libraries for combinatorial selection of replicating antigen-antibody pairs", PNAS, Feb. 3, 2009, vol. 106, doi:10.1073/pnas.0812291106, p. 1380-1385.
Kempton, et al., "Multiple Input Sensing and Signal Integration Using a Split Cas12a System", Molecular Cell, Apr. 2, 2020, p. 184-191.
Holt, et al., "By-passing selection: direct screening for antibody-antigen interactions using protein arrays", Nucleic Acids Research, Jun. 16, 2000, vol. 28, No. 15, p. 1-5.
Delley, et al., "Microfluidic particle zipper enables controlled loading of droplets with distinct particle types", Lab Chip., Jul. 14, 2020, doi:10.1039/d01c00339e, p. 2465-2472.
Betancur, et al., "miRNA-like duplexes as RNAi triggers with improved specificity", Frontiers in Genetics, vol. 3, doi: 10.3389/fgene.2012.00127, pp. 1-6, Jul. 12, 2012.
Deng, et al., "Topological barrier to Cas12a activation by circular DNA nanostructures facilitates autocatalysis and transforms DNA/RNA sensing", Nature Communications, doi.org/10.1038/s41467-024-46001-8, pp. 1-16, Mar. 5, 2024.
Koonin, et al., "Diversity, classification and evolution of CRISPR-Cas systems", Current Opinion in Microbiology, 2017, 37, pp. 67-78, Jun. 9, 2017.
Zhou, et al., "High-throughput split-protein profiling by comgining transposon mutagenesis and regulated protein-protein interactions with deep sequencing", International Journal of Biological Macromolecules, pp. 543-552, Feb. 2, 2022.
International Search Report and Written Opinion for International Application No. PCT/US23/34598, dated Feb. 8, 2024, p. 1-25.
International Search Report and Written Opinion for International Application No. PCT/US23/34231, dated Feb. 16, 2024, p. 1-19.
International Search Report and Written Opinion for International Application No. PCT/US23/33554, dated Feb. 13, 2024, p. 1-23.
International Search Report and Written Opinion for International Application No. PCT/US2024/022090, dated Jun. 12, 2024, p. 1-16.

SAMPLE SPLITTING FOR MULTIPLEXED DETECTION OF NUCLEIC ACIDS WITHOUT AMPLIFICATION

RELATED CASES

This application is a continuation of U.S. Ser. No. 18/406,159, filed 7 Jan. 2024, now allowed, which claims priority to U.S. Ser. No. 63/438,147, filed 10 Jan. 2023, both of which are incorporated by reference in their entirety.

FIELD OF THE INVENTION

The present disclosure relates to multiplexed assay methods used to detect target nucleic acids of interest from several to many source organisms in a sample without amplification of the target nucleic acids of interest. The methods involve detection of short sequences from several to many loci scattered throughout each source organism genome.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Rapid and accurate identification of, e.g., infectious agents, microbe contamination, variant nucleic acid sequences that indicate the presence of diseases such as cancer, or contamination by heterologous sources is important in order to select correct treatment; identify tainted food, pharmaceuticals, cosmetics and other commercial goods; and to monitor the environment including identification of biothreats. Classic PCR and nucleic acid-guided nuclease or CRISPR (clustered regularly interspaced short palindromic repeats) detection methods rely on pre-amplification of target nucleic acids of interest to enhance detection sensitivity. However, amplification increases time to detection and may cause changes to the relative proportion of nucleic acids in samples that, in turn, lead to artifacts or inaccurate results.

Improved technologies that allow very rapid and accurate detection of nucleic acids without amplification are therefore needed for timely diagnosis and treatment of disease, to identify toxins in consumables and the environment, as well as in other applications.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides sample preparation and multiplexed cascade assay methods to detect target nucleic acids of interest in a sample without amplification of the target nucleic acids of interest. The sample preparation methods involve sample splitting without sacrificing sensitivity. The "nucleic acid-guided nuclease cascade assays" or "signal boost cascade assays" or "cascade assays" described herein comprise two different ribonucleoprotein (RNP) complexes and blocked nucleic acid molecules, which allow for massive multiplexing. The blocked nucleic acid molecules in the cascade assay keep second ribonucleoprotein complexes (RNP2s) "locked" unless and until a target nucleic acid of interest activates the first ribonucleoprotein complexes (RNP1s). The present nucleic acid-guided nuclease cascade assay can detect target nucleic acids of interest (e.g., DNA, RNA and/or cDNA) at attamolar (aM) (or lower) limits in less than ten minutes (including sample prep) without the need for amplifying the target nucleic acid(s) of interest, thereby avoiding the drawbacks of multiplex DNA amplification, such as primer-dimerization. A particularly advantageous feature of the cascade assay is that, with the exception of the gRNAs in RNP1, the cascade assay components may be the same in each assay no matter what target nucleic acids of interest are being detected; moreover, the gRNAs in the RNP1 are easily reprogrammed using traditional guide design methods.

Thus, one embodiment provides a method for preparing a detection substrate for detecting one or more target nucleic acids of interest from two or more source organisms in a sample comprising the steps of: obtaining a sample; providing a detection substrate comprising partitions; lysing the source organisms and fractionating nucleic acids obtained from the lysed source organisms in the sample, wherein the nucleic acids are fractionated into lengths of 30 bp to 50,000 bp; designing a plurality of first guide nucleic acids (gRNA1s) complementary to a plurality of loci (e.g., at least two, three, four, five, six, seven, eight, nine, ten, fifteen, twenty, twenty-five or fifty loci) in each genome of the two or more source organisms; forming first ribonucleoprotein complexes (RNP1s) in the partitions in the detection substrate, wherein the RNP1s comprise a first nucleic acid-guided nuclease and the gRNA1s, wherein the first nucleic acid-guided nuclease exhibits both cis- and trans-cleavage activity, and wherein the RNP1s are formed in partitions where different partitions comprise different gRNA1 sequences; and adding the fractionated nucleic acids obtained from the lysed source organisms in the sample to each partition.

In some aspects, the RNP1s comprise a nucleic acid-guided nuclease selected from Cas3, Cas12a, Cas12b, Cas12c, Cas12d, Cas12e, Cas14, Cas12h, Cas12i, Cas12j, Cas13a, or Cas13b.

In some aspects, the lysing step is performed at 95° C.; in some aspects, the lysing step is performed using bead beating; in some aspects, the lysing step is performed by sonication, and in some aspects, the lysing step is performed by a combination of two of these methods. In some aspects, a lysing buffer comprises one or more reducing agent and/or a chaotropic salt and in some aspects, the lysing buffer comprises EDTA, TCEP or DTT, or guanidine isothiocyanate. In some aspects, nucleic acid purification is performed after lysis.

In some aspects, the partitions in the detection substrate are wells and in other aspects, the partitions in the detection substrate are defined areas separated by interstitial regions.

In some aspects, the nucleic acids are fractionated into lengths of 500 bp to 500,000 bp, or 100 bp to 250,000, or 100 bp to 100,000, or 50 bp to 50,000 bp, or 100 bp to 10,000 bp, or 100 bp to 5000 bp, or 30 bp to 1000 bp, or 30 bp to 100 bp.

In some aspects, the method further comprises the steps of: providing a reaction mixture comprising: second ribonucleoprotein complexes (RNP2s) comprising a second nucleic acid-guided nuclease and a second gRNA that is not complementary to the target nucleic acids of interest, wherein the second nucleic acid-guided nuclease exhibits both cis- and trans-cleavage activity; and a plurality of blocked nucleic acid molecules comprising a sequence corresponding to the second gRNA, wherein the blocked nucleic acid molecules comprise: a first region recognized by the RNP2 complex; one or more second regions not complementary to the first region forming at least one loop; and one or more third regions complementary to and hybridized to the first region forming at least one clamp; and adding the reaction mixture to each partition.

In some aspects, the reaction mixture further comprises a reporter moiety, wherein the reporter moiety comprises a DNA, RNA or chimeric nucleic acid molecule, where in some aspects, the reporter moiety is not operably linked to the blocked nucleic acid molecule; however, in other aspects, the reporter moiety is operably linked to the blocked nucleic acid molecules.

Also provided is a method for identifying one or more target nucleic acids of interest from two or more source organisms in a sample comprising the steps of: obtaining a sample; lysing the source organisms and fractionating nucleic acids obtained from the lysed source organisms in the sample, wherein the nucleic acids are fractionated into lengths of 100 bp to 50,000 bp; designing a plurality of first guide nucleic acids (gRNA1s) complementary to a plurality of loci (e.g., at least two, three, four, five, six, seven, eight, nine, ten, fifteen, twenty, twenty-five or fifty loci) in each genome of the two or more source organisms; forming first ribonucleoprotein complexes (RNP1s) comprising a first nucleic acid-guided nuclease and the gRNA1s, wherein the first nucleic acid-guided nuclease exhibits both cis- and trans-cleavage activity and wherein the RNP1s are formed in partitions where different partitions comprise different gRNA1 sequences; providing a reaction mixture comprising: second ribonucleoprotein complexes (RNP2s) comprising a second nucleic acid-guided nuclease and a second gRNA that is not complementary to the target nucleic acids of interest, wherein the second nucleic acid-guided nuclease exhibits both cis- and trans-cleavage activity; and a plurality of blocked nucleic acid molecules comprising a sequence corresponding to the second gRNA, wherein the blocked nucleic acid molecules comprise: a first region recognized by the RNP2 complex; one or more second regions not complementary to the first region forming at least one loop; and one or more third regions complementary to and hybridized to the first region forming at least one clamp; contacting the RNP1s in each partition with the reaction mixture and the fractionated nucleic acids in the sample under conditions that allow the target nucleic acids of interest in the sample to bind to RNP1, wherein upon binding of target nucleic acids of interest the RNP1s become active initiating trans-cleavage of at least one of the plurality of blocked nucleic acid molecules thereby producing at least one unblocked nucleic acid molecule and wherein the at least one unblocked nucleic acid molecule binds to RNP2 initiating trans-cleavage of at least one further blocked nucleic acid molecule; and detecting cleavage products from each partition, thereby detecting the target nucleic acids of interest in the sample.

In some aspects, one or both of RNP1 and RNP2 comprise a nucleic acid-guided nuclease selected from Cas3, Cas12a, Cas12b, Cas12c, Cas12d, Cas12e, Cas14, Cas12h, Cas12i, Cas12j, Cas13a, or Cas13b.

In some aspects, the reaction mixture further comprises a reporter moiety, and in some aspects, the reporter moiety is a fluorescent, chemiluminescent, radioactive, colorimetric or other optical signal. In some aspects, the reporter moiety is not operably linked to the blocked nucleic acid molecule; however, in other aspects, the reporter moiety is operably linked to the blocked nucleic acid molecule.

In some aspects, the lysing step is performed at 95° C., using bead beating or sonication, or a combination thereof. In some aspects, a lysing buffer comprises one or more reducing agent and/or a chaotropic salt and in some aspects, the lysing buffer comprises EDTA, TCEP or DTT, or guanidine isothiocyanate. In some aspects, nucleic acid purification is performed after lysis.

In some aspects, the partitions are wells and in other aspects, the partitions are spots separated by interstitial regions.

In some aspects, the nucleic acids are fractionated into lengths of 500 bp to 500,000 bp, or 100 bp to 250,000 bp, or 100 bp to 100,000 bp, or 50 bp to 50,000 bp, or 100 bp to 10,000 bp, or 100 bp to 5000 bp, or 30 bp to 1000 bp, or 30 bp to 100 bp.

These aspects and other features and advantages of the invention are described below in more detail.

BRIEF DESCRIPTION OF THE DRAWINGS

The foregoing and other features and advantages of the present invention will be more fully understood from the following detailed description of exemplary embodiments taken in conjunction with the accompanying drawings in which.

It should be understood that the drawings are not necessarily to scale, and that like reference numbers refer to like features.

DEFINITIONS

Figure 1A:
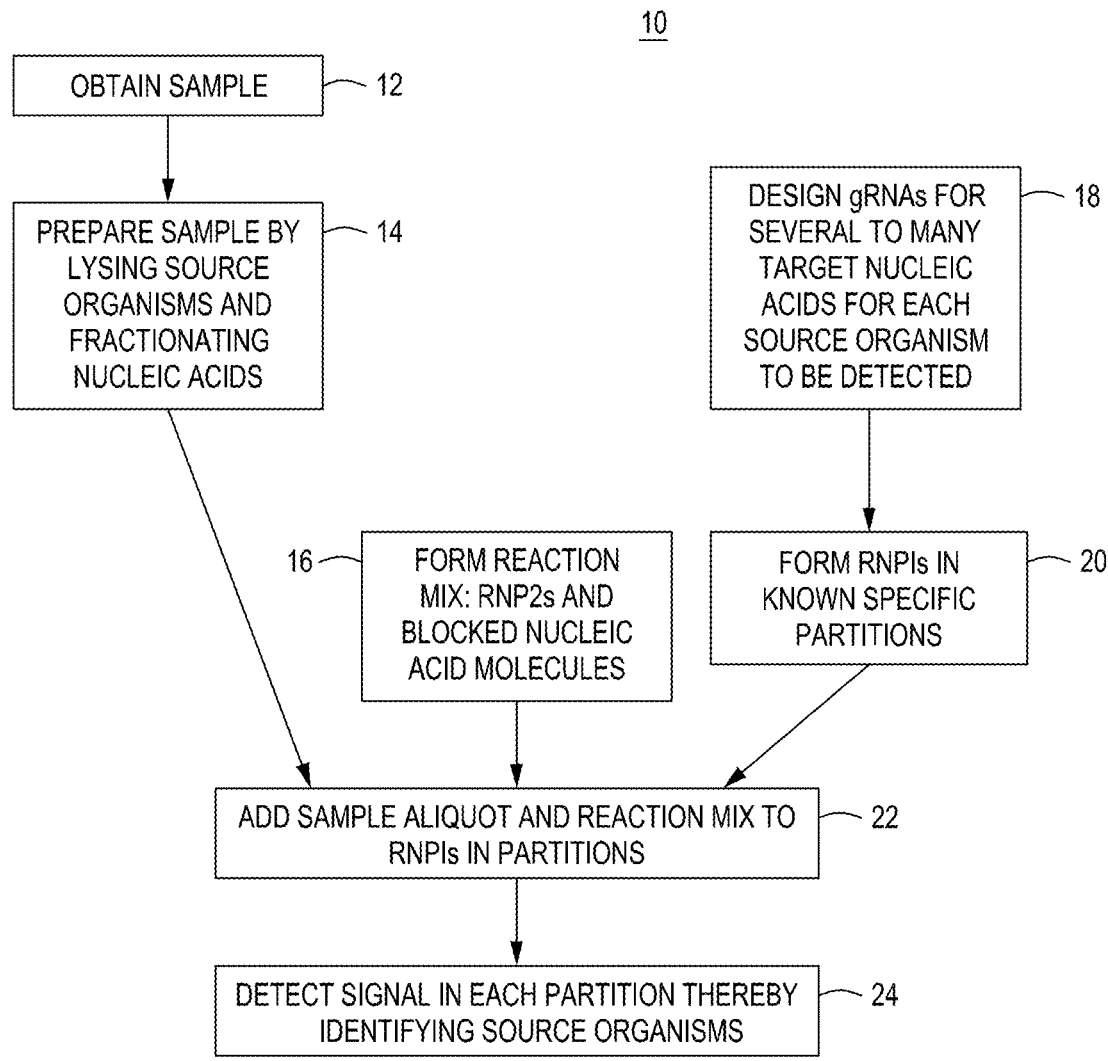
FIG. 1A is a flow chart of the general principle underlying the embodiments of the sample preparation and cascade assay described herein.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

All of the functionalities described in connection with one embodiment of the compositions and/or methods described herein are intended to be applicable to the additional embodiments of the compositions and/or methods except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

Note that as used herein and in the appended claims, the singular forms "a," "an," and "the" include plural referents unless the context clearly dictates otherwise. Thus, for example, reference to "a cell" refers to one or more cells, and reference to "a system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention. Conventional methods are used for the procedures described herein, such as those provided in the art, and demonstrated in the Examples and various general references. Unless otherwise stated, nucleic acid sequences described herein are given, when read from left to right, in the 5' to 3' direction. Nucleic acid sequences may be provided as DNA, as RNA, or a combination of DNA and RNA (e.g., a chimeric nucleic acid).

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both limits, ranges excluding either or both of those included limits are also included in the invention.

The term "and/or" where used herein is to be taken as specific disclosure of each of the multiple specified features or components with or without another. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "about," as applied to one or more values of interest, refers to a value that falls within 10%, 9%, 8%, 7%, 6%, 5%, 4%, 3%, 2%, 1%, or less in either direction (greater than or less than) of a stated reference value, unless otherwise stated or otherwise evident from the context.

As used herein, the terms "binding affinity" or "dissociation constant" or "$K_d$" refer to the tendency of a molecule to bind (covalently or non-covalently) to a different molecule. A high $K_d$ (which in the context of the present disclosure refers to blocked nucleic acid molecules binding to RNP2) indicates the presence of more unbound molecules, and a low $K_d$ (which in the context of the present disclosure refers to unblocked nucleic acid molecules binding to RNP2) indicates the presence of more bound molecules. In the context of the present disclosure and the binding of blocked or unblocked nucleic acid molecules to RNP2, low $K_d$ values are in a range from about 100 fM to about 1 aM or lower (e.g., 100 zM) and high $K_d$ values are in the range of 100 nM-100 μM (10 mM) and thus are about $10^5$- to $10^{10}$-fold or higher as compared to low $K_d$ values.

As used herein, the terms "binding domain" or "binding site" refer to a region on a protein, DNA, or RNA, to which specific molecules and/or ions (ligands) may form a covalent or non-covalent bond. By way of example, a polynucleotide sequence present on a nucleic acid molecule (e.g., a primer binding domain) may serve as a binding domain for a different nucleic acid molecule. Characteristics of binding sites are chemical specificity, a measure of the types of ligands that will bond, and affinity, which is a measure of the strength of the chemical bond.

As used herein, the term "blocked nucleic acid molecule" refers to nucleic acid molecules that cannot bind to the first or second RNP complex to activate cis- or trans-cleavage. "Unblocked nucleic acid molecule" refers to a formerly blocked nucleic acid molecule that has been unblocked and can bind to the second RNP complex (RNP2) to activate trans-cleavage of additional blocked nucleic acid molecules.

The terms "Cas RNA-guided nucleic acid-guided nuclease" or "CRISPR nuclease" or "nucleic acid-guided nuclease" refer to a CRISPR-associated protein that is an RNA-guided nucleic acid-guided nuclease suitable for assembly with a sequence-specific gRNA to form a ribonucleoprotein (RNP) complex.

As used herein, the terms "cis-cleavage", "cis-nucleic acid-guided nuclease activity", "cis-mediated nucleic acid-guided nuclease activity", "cis-nuclease activity", "cis-mediated nuclease activity", and variations thereof refer to sequence-specific cleavage of a target nucleic acid of interest in the case of RNP1 and an unblocked nucleic acid molecule in the case of RNP2 by a nucleic acid-guided nuclease in an RNP complex. Cis-cleavage is a single turn-over cleavage event in that only one substrate molecule is cleaved per event.

The term "complementary" as used herein refers to Watson-Crick base pairing between nucleotides and specifically refers to nucleotides hydrogen-bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10, or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-ATCGAT-5' is 100% complementary to a region of the nucleotide sequence 5'-GCTAGCTAG-3'.

As used herein, the term "contacting" refers to placement of two moieties in direct physical association, including in solid or liquid form. Contacting can occur in vitro with isolated cells (for example in a tissue culture dish or other vessel) or in samples or in vivo by administering an agent to a subject.

A "control" is a reference standard of a known value or range of values.

The terms "guide nucleic acid" or "guide RNA" or "gRNA" refer to a polynucleotide comprising 1) a crRNA region or guide sequence capable of hybridizing to the target strand of a target nucleic acid of interest, and 2) a scaffold sequence capable of interacting or complexing with a nucleic acid-guided nuclease. The crRNA region of the gRNA is a customizable component that enables nucleic acid binding specificity in every nucleic acid-guided nuclease reaction. A gRNA can include any polynucleotide sequence having sufficient complementarity with a target nucleic acid of interest in the case of RNP1 or an unblocked nucleic acid molecule in the case of RNP2 to hybridize with the target nucleic acid of interest or unblocked nucleic acid molecule and to direct sequence-specific binding and cleavage by an RNP.

"Modified" refers to a changed state or structure of a molecule. Molecules may be modified in many ways including chemically, structurally, and functionally. In one embodiment, a nucleic acid molecule (for example, a blocked nucleic acid molecule) may be modified by the introduction of non-natural nucleosides, nucleotides, and/or internucleoside linkages. In another embodiment, a modified protein (e.g., a modified or variant nucleic acid-guided nuclease) may refer to any polypeptide sequence alteration which is different from the wildtype.

As used herein, a "partition" is an isolate region (e.g., a feature surrounded by an interstitial region) or an isolate depression (e.g., a well) on a substrate, or a droplet. Partitions are used, in relation to the present disclosure, to separate a plurality of ribonucleoprotein complexes (RNP1s) comprising different guide nucleic acids (gRNA1s) into compartments (e.g., separate wells, features, or droplets). Partitions may be disposed upon a detection substrate.

The terms "percent sequence identity", "percent identity", or "sequence identity" refer to percent (%) sequence identity with respect to a reference polynucleotide or polypeptide sequence following alignment by standard techniques. Alignment for purposes of determining percent sequence identity can be achieved in various ways that are within the capabilities of one of skill in the art, for example, using publicly available computer software such as BLAST, BLAST-2, PSI-BLAST, or Megalign software. In some embodiments, the software is MUSCLE (Edgar, Nucleic Acids Res., 32 (5): 1792-1797 (2004)). Those skilled in the art can determine appropriate parameters for aligning sequences, including any algorithms needed to achieve maximal alignment over the full length of the sequences being compared. For example, in embodiments, percent sequence identity values are generated using the sequence comparison computer program BLAST (Altschul, et al., J. Mol. Biol., 215:403-410 (1990)).

As used herein, the terms "preassembled ribonucleoprotein complex", "ribonucleoprotein complex", "RNP complex", or "RNP" refer to a complex containing a guide RNA (gRNA) and a nucleic acid-guided nuclease, where the gRNA is integrated with the nucleic acid-guided nuclease. The gRNA, which includes a sequence complementary to a target nucleic acid of interest, guides the RNP to the target nucleic acid of interest and hybridizes to it. The hybridized target nucleic acid/gRNA units are cleaved by the nucleic acid-guided nuclease. In the cascade assays described herein, a first ribonucleoprotein complex (RNP1) includes a first guide RNA (gRNA) specific to a target nucleic acid of interest, and a first nucleic acid-guided nuclease, such as, for example, cas12a or cas14a for a DNA target nucleic acid, or cas13a for an RNA target nucleic acid. A second ribonucleoprotein complex (RNP2) used for signal amplification includes a second guide RNA specific to an unblocked nucleic acid and a second nucleic acid-guided nuclease, which may be different from or the same as the first nucleic acid-guided nuclease.

As used herein, the terms "protein" and "polypeptide" are used interchangeably. Proteins may or may not be made up entirely of amino acids.

As used herein, the term "sample" refers to tissues; cells or component parts; body fluids, including but not limited to peripheral blood, serum, plasma, ascites, urine, cerebrospinal fluid (CSF), sputum, saliva, bone marrow, synovial fluid, aqueous humor, amniotic fluid, cerumen, breast milk, bronchoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. "Sample" may also refer to specimens or aliquots from food; agricultural products; pharmaceuticals; cosmetics; nutraceuticals; personal care products; environmental substances such as soil, water (from both natural and treatment sites), air, or sewer samples; industrial sites and products; and chemicals and compounds. A sample further may include a homogenate, lysate or extract. A sample further refers to a medium, such as a nutrient broth or gel, which may contain cellular components, such as proteins or nucleic acid molecules.

The terms "target nucleic acid of interest", "target sequence", "target nucleic acid molecule of interest", "target molecule of interest", "target nucleic acid", or "target of interest" refer to any locus that is recognized by a gRNA sequence in vitro or in vivo. The "target strand" of a target nucleic acid of interest is the strand of the double-stranded target nucleic acid that is complementary to a gRNA. The spacer sequence of a gRNA may be 50%, 60%, 75%, 80%, 85%, 90%, 95%, 97.5%, 98%, 99% or more complementary to the target nucleic acid of interest. Optimal alignment can be determined with the use of any suitable algorithm for aligning sequences. Full complementarity is not necessarily required provided there is sufficient complementarity to cause hybridization and trans-cleavage activation of an RNP complex. The target nucleic acid of interest may be present in a sample, such as a biological or environmental sample, and it can be a viral nucleic acid molecule, a bacterial nucleic acid molecule, a fungal nucleic acid molecule, or a polynucleotide of another organism, such as a coding or a non-coding sequence, and it may include single-stranded or double-stranded DNA molecules, such as a cDNA or genomic DNA, or RNA molecules, such as mRNA, tRNA, and rRNA. The target nucleic acid of interest may be associated with a protospacer adjacent motif (PAM) sequence, which may include a 2-5 base pair sequence adjacent to the protospacer. In some embodiments 1, 2, 3, 4, 5, 6, 7, 8, 9, 10, or more target nucleic acids can be detected by the disclosed method.

As used herein, the terms "trans-cleavage", "trans-nucleic acid-guided nuclease activity", "trans-mediated nucleic acid-guided nuclease activity", "trans-nuclease activity", "trans-mediated nuclease activity" and variations thereof refer to indiscriminate, non-sequence-specific cleavage of a target nucleic acid molecule by a nucleic acid-guided nuclease (such as by a Cas12, Cas13, and Cas14) which is triggered by binding of N nucleotides of a target nucleic acid molecule to a gRNA in an RNP. Trans-cleavage is a "multiple turn-over" event, in that more than one substrate molecule is cleaved after initiation by a single turn-over cis-cleavage event.

Type V CRISPR/Cas nucleic acid-guided nucleases are a subtype of Class 2 CRISPR/Cas effector nucleases such as, but not limited to, engineered Cas12a, Cas12b, Cas12c, C2c4, C2c8, C2c5, C2c10, C2c9, CasX (Cas12c), CasY (Cas12d), Cas 13a nucleases or naturally-occurring proteins, such as a Cas12a isolated from, for example, *Francisella tularensis* subsp. *novicida* (Gene ID: 60806594), *Candidatus Methanoplasma termitum* (Gene ID: 24818655), *Candidatus Methanomethylophilus* alvus (Gene ID: 15139718), and [*Eubacterium*] *eligens* ATCC 27750 (Gene ID: 41356122), and an artificial polypeptide, such as a chimeric protein.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like.

DETAILED DESCRIPTION

The present disclosure provides compositions of matter and methods for cascade assays that detect nucleic acids. First, neither the sample preparation methods nor the cascade assays require amplification of the target nucleic acids and yet the methods and arrays retain sensitivity. The cascade assays allow for massive multiplexing, and provide low cost, minimum workflow and results in less than ten minutes, including the time for sample prep. The cascade assays described herein comprise first and second ribonucleoprotein complexes and blocked nucleic acid molecules. The blocked nucleic acid molecules keep the second ribonucleoprotein complexes (RNP2s) "locked" unless and until a target nucleic acid of interest activates the first ribonucleoprotein complexes (RNP1s). The methods comprise the steps of designing guide nucleic acids specific to several to many loci in the genome of the one or more source organisms, synthesizing first ribonucleoprotein complexes in partitions, providing cascade assay components, combining the cascade assay components and prepped sample, distributing the cascade assay components and prepped sample into the partitions, and detecting a signal that is generated if a target nucleic acid of interest is present in the sample.

Early and accurate identification of, e.g., infectious agents, microbe contamination, variant nucleic acid sequences that indicate the presence of diseases such as cancer or contamination by heterologous sources is important in order to: select correct treatment; identify tainted food, pharmaceuticals, cosmetics and other commercial goods; and to monitor the environment. Nucleic acid-guided nucleases, such as Type V nucleic acid-guided nucleases, can be utilized for the detection of target nucleic acids of interest associated with diseases, food contamination and environmental threats by exploiting the property of transcleavage. However, currently available nucleic acid detection such as quantitative PCR (also known as real time PCR or qPCR) or CRISPR-based detection assays such as SHERLOCK™ and DETECTR™ rely on DNA amplification, which requires time and may lead to changes to the relative proportion of nucleic acids, particularly in multiplexed nucleic acid assays. The lack of rapidity for these detection assays is due to the fact that there is a significant lag phase early in the amplification process where fluorescence above background cannot be detected. With qPCR, for example, there is a lag until the cycle threshold or Ct value, which is the number of amplification cycles required for the fluorescent signal to exceed the background level of fluorescence, is achieved and can be quantified.

The present disclosure describes sample preparation and a signal boost cascade assay that can detect several to many to massively multiplexed target nucleic acids of interest from several to many source organisms (e.g., DNA, RNA and/or cDNA) in a multiplexed manner at attamolar (aM) (or lower) limits in less than ten minutes including sample prep without the need for amplifying the target nucleic acid(s) of interest, thereby avoiding the drawbacks of multiplex amplification, such as primer-dimerization. As described in detail below, the sample preparation techniques utilize assaying for multiple loci in a genome from each of two to hundreds of source organisms. The cascade assays utilize signal boost mechanisms comprising various components including nucleic acid-guided nucleases; guide RNAs (gRNAs) incorporated into ribonucleoprotein complexes (RNP complexes); blocked nucleic acid molecules, and reporter moieties. A particularly advantageous feature of the cascade assay is that, with the exception of the gRNAs in the RNP1s (i.e., gRNA1s), the cascade assay components may be identical no matter what target nucleic acids of interest are being detected, and gRNA1 is easily programmable using known techniques and gRNA design tools known in the art.

The cascade assay provides a reaction mix comprising: a first ribonucleoprotein complex (RNP1) comprising a first Cas enzyme that exhibits both cis- and trans-cleavage activity and several to many first gRNAs; a second ribonucleoprotein complex (RNP2) comprising a second Cas enzyme that also exhibits both cis- and trans-cleavage activity and a second gRNA; blocked nucleic acid molecules; and reporter moieties, which may be separate molecules from the blocked nucleic acid molecules or the reporter moieties may be incorporated into and part of the blocked nucleic acid molecules. RNP1 is not activated unless a target nucleic acid molecule is detected and bound.

FIG. 1A is a flow chart of the general principle underlying the embodiments of the sample preparation methods and cascade assays described herein. Details related to each step outlined in FIG. 1A are described in more detail below in relation to FIGS. 1B and 2A. Method (10) begins with obtaining a sample (12). As described in detail below, a sample can be taken from any number of sources such as biological samples including blood, serum, plasma, saliva, mucus, a nasal swab, a nasal pharyngeal swab, a buccal swab, a cell, a cell culture, and tissue from any mammal, such as, but not limited to, a human, primate, monkey, cat, dog, mouse, pig, cow, horse, sheep, and bat. Samples may also be obtained from any other source, such as air, water, soil, surfaces, food, beverages, nutraceuticals, clinical sites or products, industrial sites (including food processing sites) and products, plants and grains, cosmetics, personal care products, pharmaceuticals, medical devices, agricultural equipment and sites, and commercial products or processing facilities.

Once the sample is obtained, it is prepared (14) where source organisms (e.g., cells of source organisms) present in the sample such as bacteria, viruses, fungi or other organisms are lysed and the nucleic acids from these source organisms are fractionated into lengths of nucleic acids approximately 500 bp to 500,000 bp, or 100 to 250,000 bp, or 100 bp to 100,000 bp, or 50 bp to 50,000 bp, or 100 bp to 10,000 bp, or 100 bp to 5,000 bp, or 30 bp to 1,000 bp, or 30 bp to 100 bp depending on the specific preparation used. The temperature maybe increased to 95° C. during preparation or during elution of the nucleic acids during purification. It has been demonstrated that heating E. coli DNA at 95° C. for 5 minutes results in fragment sizes of 500 bp-1000 bp (see Yang and Hang, J. of Biomolecular Techniques, 24:98-103 (2013)). Human DNA fragments appear as a smear from 650 bp-12,000 bp when heated at 95° C. for 2 minutes, while 18 minutes of heating resulted in a smear ranging from 100 bp-500 bp. In addition to heating, sonication or bead beating may be used for DNA shearing; alternatively, enzymatic fragmentation may be employed.

In another step and separately, a reaction mix is formed (16) comprising the second ribonucleoprotein complexes (RNP2s) comprising a second guide nucleic acid (i.e., gRNA2) and a second nucleic acid nuclease, and the reaction mix further comprises blocked nucleic acids. FIG. 1C provides a high-level overview of the cascade assay utilizing the aforementioned assay components, and FIG. 2A and the accompanying description provides details of embodiments of the cascade assay. The reaction mix comprises the assay components aside from the first ribonucleoprotein complexes (RNP1s).

In yet another step and separately, first gRNAs (gRNA1s) are designed to target several to many loci (e.g., at least two, three, four, five, six, seven, eight, nine, ten, fifteen, twenty, twenty-five or fifty loci) in the genomes of each source organism to be detected (18). That is, e.g., ten gRNA Is may be designed to detect source organism X (e.g., gRNA1-X1; gRNA1-X2; gRNA1-X3; gRNA1-X4, and so on up to gRNA1-X10); ten gRNA1s may be designed to detect source organism Y (e.g., gRNA1-Y1; gRNA1-Y2; gRNA1-Y3; gRNA1-Y4, and so on up to gRNA1-Y10); and ten gRNA1s may be designed to detect source organism Z (e.g., gRNA1-Z1; gRNA1-Z2; gRNA1-Z3; gRNA1-Z4, and so on up to gRNA1-Z10). These gRNA1s are distributed into partitions of known position and ribonucleoprotein complexes (i.e., RNP1s) are formed (20) using a first nucleic acid-guided nuclease and the gRNA1s. Alternatively, the RNP1s may be formed with the gRNA1s in separate partitions (e.g., Eppendorf tubes), then distributed into partitions for the reaction.

The different gRNA1s can be partitioned as desired; for example, all gRNA1s for source organism X may reside in the same partition, all gRNA1s for source organism Y may reside in the same partition but a different partition from the gRNA1s for source organism X, and all gRNA Is for source organism Z may reside in the same partition but in a different partition from the partitions where the gRNA1s for source organisms X and Y reside. Alternatively, all gRNA1s for source organism X may reside in partition A, all gRNA1s for source organism Y may reside in the same partition and in the same partition A as the gRNA Is for source organism X, and all gRNA1s for source organism Z may reside in the same partition but in a different partition B from the gRNA1s for source organisms X and Y. The number of partitions will depend on the size of the sample and the number of source organisms to be detected and the number of genomic fragments interrogated from each source organism. As described below, as many as 10,000 or more different nucleic acids may be detected in the cascade assays; thus, for example, if there are 100 different source organisms to be detected and gRNA1s are designed to, e.g., 10 different loci on each genome of each source organism, the cascade assay will be configured to detect 1000 sequences.

Once the sample has been prepared, the reaction mixture has been prepared, and the RNP1s are formed in known partitions, these elements are combined (22) where the reaction mixture and sample aliquots are added to the partitions and reaction conditions are provided for the cascade assay to take place. As discussed below, even at ambient temperatures of about 16-20° C., or less up to 48° C. the cascade assay can detect source organisms present in the sample. The source organisms are detected via a signal reporter moiety in the partitions. Note that in the method described above, the first ribonucleoproteins (RNP1s) comprising the first nucleic acid-guided nuclease and the first guide nucleic acids (gRNA1s) are partitioned and the reaction mix comprising the other assay components are added to the partition along with the sample. In an alternative embodiment, the gRNA1s may be in the partitions and the first nucleic acid-guided nuclease may be part of the reaction mix along with the other assay components. In this case, the RNP1s will form in the partitions in a mix with the other assay components. Although this alternative is viable, because a goal of the present methods is rapid detection of source organisms, it is preferable that the RNP1s are preformed in the absence of other reaction mixture reagents to speed reaction kinetics.

Figure 1B:
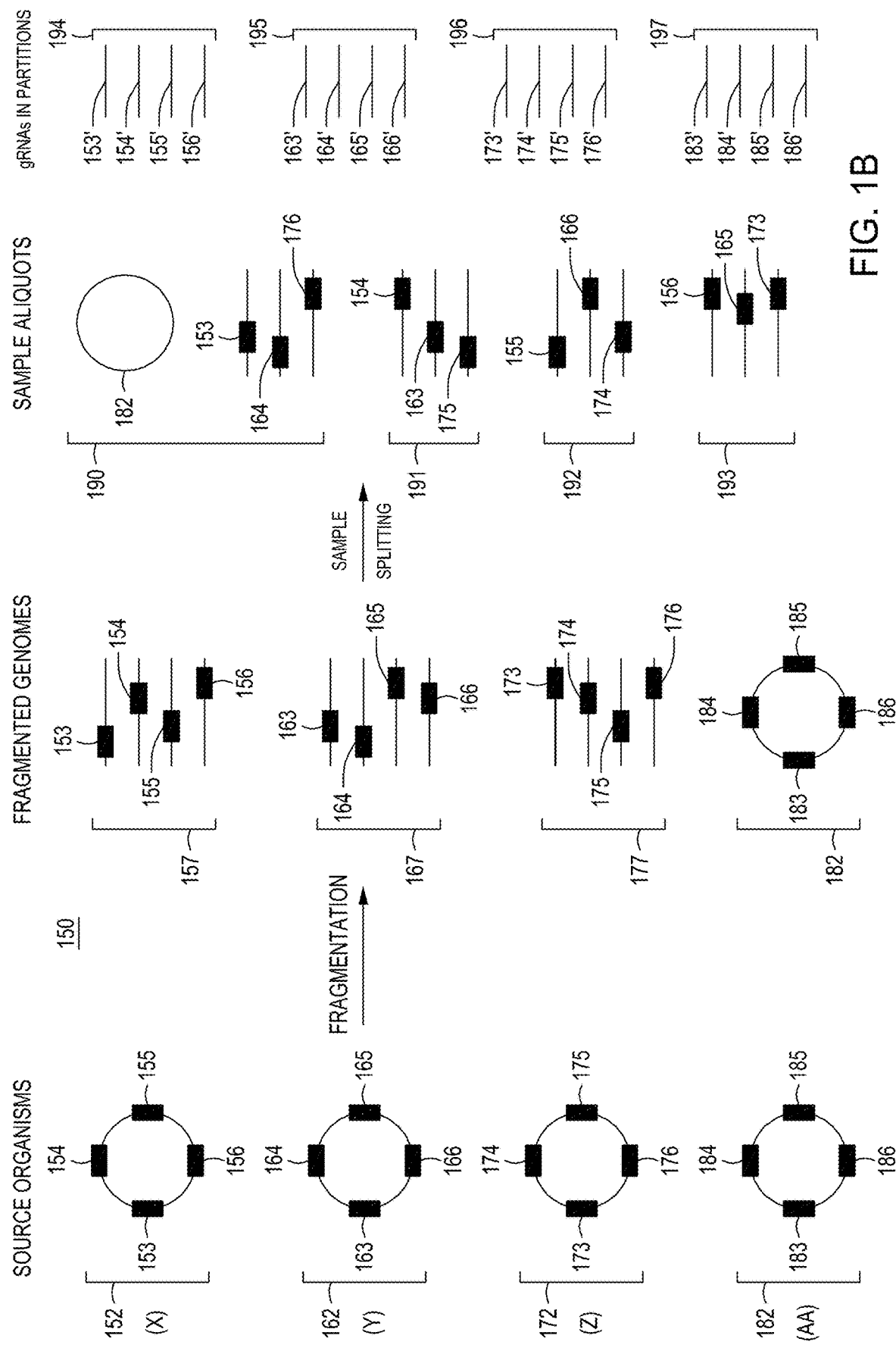
FIG. 1B is an overview of the principles behind the sample splitting methods of the present disclosure.
Figure 1C:
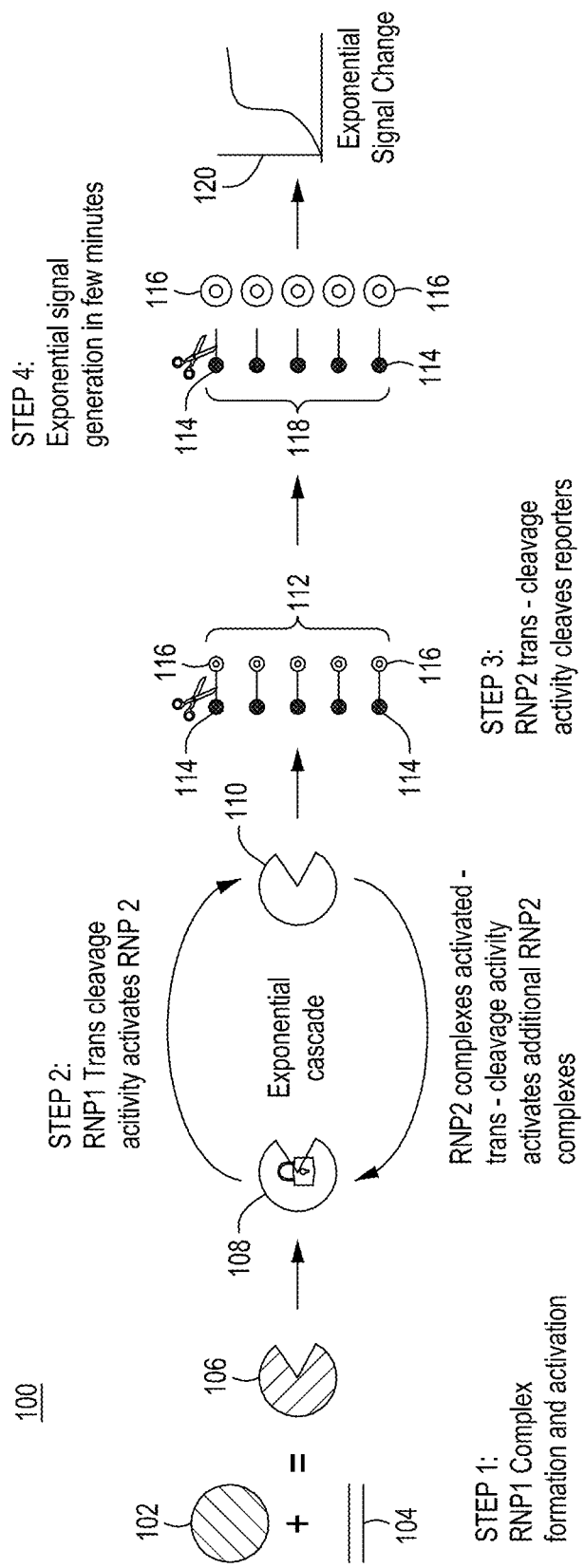
FIG. 1C is an overview of the general principles underlying the nucleic acid-guided nuclease cascade assay described in detail herein, where target nucleic acids of interest from a sample do not need to be amplified before detection.

FIG. 1B shows an overview of the principles behind the sample splitting/multiplexing methods of the present disclosure. Because the present cascade assay methods do not involve amplification of the nucleic acids from source organisms, other approaches may be used to increase assay sensitivity. As described generally in FIG. 1A, the sample splitting/multiplexing methods described herein include the steps of shearing or fragmenting the nucleic acids obtained from the genomes of the source organisms in a sample and designing several to many first guide nucleic acids (gRNA1s) specific for different loci from each source organism.

FIG. 1B is a schematic overview (150) of the general principle underlying sample splitting and gRNA1 multiplexing. At left in FIG. 1B are seen four exemplary source organisms, e.g., source organism X (with genome 152), source organism Y (with genome 162), source organism Z (with genome 172), and source organism AA (with genome 182). Each genome (152, 162, 172, and 182) of each source organism (X, Y, Z and AA, respectively) comprises four genomic loci (153, 154, 155, and 156; 163, 164, 165, and 166; 173, 174, 175, and 176; and 183, 184, 185 and 186, respectively) that will be interrogated by the first ribonucleoprotein complexes (RNP1s). That is, the first ribonucleoprotein complexes (RNP1s) comprise four different first guide nucleic acids (gRNA1s) for each of the four source organisms, each different gRNA1 corresponding to one of the four genomic loci; thus, in this example, there will be sixteen different RNP1s, four for each source organism.

During sample preparation (step (14) of FIG. 1A), the source organisms are lysed and the nucleic acids from the source organisms are fragmented, resulting in fragments (157) from genome (152) from source organism X, fragments (167) from genome (162) from source organism Y, and fragments (177) from genome (172) from source organism Z; however, for the purpose of demonstration of the principle of splitting and multiplexing, imagine genome (182) of source organism AA is not fragmented. Lysing and fragmentation results in a pool of fragmented nucleic acids from the sample except for source organism AA, where the genomic nucleic acids 182 remain unfragmented. In a next step, the sample is split and aliquots of the sample (190, 191, 192, and 193) are distributed into partitions (194, 195, 196, and 197). Partition (194) comprises gRNA1s (153', 154', 155', and 156') specific for fragments (153, 154, 155, and 156) from genome (152) of source organism X; partition (195) comprises gRNA1s (163', 164', 165', and 166') specific for fragments (163, 164, 165, and 166) from genome (162) of source organism Y; partition (196) comprises gRNA1s (173', 174', 175', and 176') specific for fragments (173, 174, 175, and 176) from genome (172) of source organism Z; and partition (197) comprises gRNA1s (183', 184', 185', and 186') specific for fragments (183, 184, 185, and 186) from genome (182) of source organism AA.

Aliquot (190) is distributed into partition (194). Because aliquot (190) comprises fragment (153) from genome (152), source organism X is detected by gRNA1 (153') in partition (194). Aliquot (191) is distributed into partition (195). Because aliquot (191) comprises fragment (163) from genome (162), source organism Y is detected by gRNA1 (163') in partition (195). Aliquot (192) is distributed into partition (196). Because aliquot (192) comprises fragment (174) from genome (172), source organism Z is detected by gRNA1 (174') in partition (196). Aliquot (193) is distributed into partition (197). Aliquot (193) does not comprise a fragment that corresponds to genome (182) of source organism AA and thus source organism AA is not detected by any gRNA1 (183', 184', 185', or 186') in partition (197). Source organism (182) was not fragmented, therefore all genomic loci (183, 184, 185 and 186) remained on the genome (182) of source organism AA, which was in aliquot (190) distributed into partition (194) comprising the gRNA1s for source organism X. Because the genome (182) for source organism AA was not fragmented, source organism AA would have only been detected if aliquot (190) had been distributed into partition (197). Note that a sample will contain several to many genome copies from the source organisms in the sample depending on the prevalence of a particular source organism in the sample; therefore, there will be several to many copies of each fragment from these genomes.

FIG. 1C provides a simplified diagram demonstrating a method (100) of a cascade assay. The cascade assay is initiated when the target nucleic acid of interest (104) binds to and activates a first pre-assembled ribonucleoprotein complex (RNP1) (102). A ribonucleoprotein (RNP) complex comprises a guide RNA (gRNA) and a nucleic acid-guided nuclease, where the gRNA is integrated with the nucleic acid-guided nuclease. The gRNA, which includes a sequence complementary to the target nucleic acid of interest, guides an RNP complex to the target nucleic acid of interest and hybridizes to it. Typically, preassembled RNP complexes are employed in the reaction mix—as opposed to separate nucleic acid-guided nucleases and gRNAs—to facilitate rapid (and in the present cascade assays, virtually instantaneous) detection of the target nucleic acid(s) of interest.

"Activation" of RNP1 refers to activating trans-cleavage activity of the nucleic acid-guided nuclease in RNP1 (106) by binding of the target nucleic acid of interest to the gRNA of RNP1, initiating cis-cleavage where the target nucleic acid of interest is cleaved by the nucleic acid-guided nuclease. This binding and/or cis-cleavage activity then initiates trans-cleavage activity (i.e., multi-turnover activity) of the nucleic acid-guided nuclease, where trans-cleavage is indiscriminate, leading to non-sequence-specific cutting of nucleic acid molecules by the nucleic acid-guided nuclease of RNP1 (106). This trans-cleavage activity triggers activation of blocked ribonucleoprotein complexes (RNP2s) (108), described in detail below. Each newly activated RNP2 (110) activates more RNP2s (108→110), which in turn cleave reporter moieties (112). The reporter moieties (112) may be a synthetic molecule linked or conjugated to a quencher (114) and a fluorophore (116) such as, for example, a probe with a dye label (e.g., FAM or FITC) on the 5' end and a quencher on the 3' end. The quencher (114) and fluorophore (116) can be about 20-30 bases apart (or about 10-11 nm apart) or less for effective quenching via fluorescence resonance energy transfer (FRET). Reporter moieties in various configurations also are described in greater detail below in FIG. 3.

Figure 3:
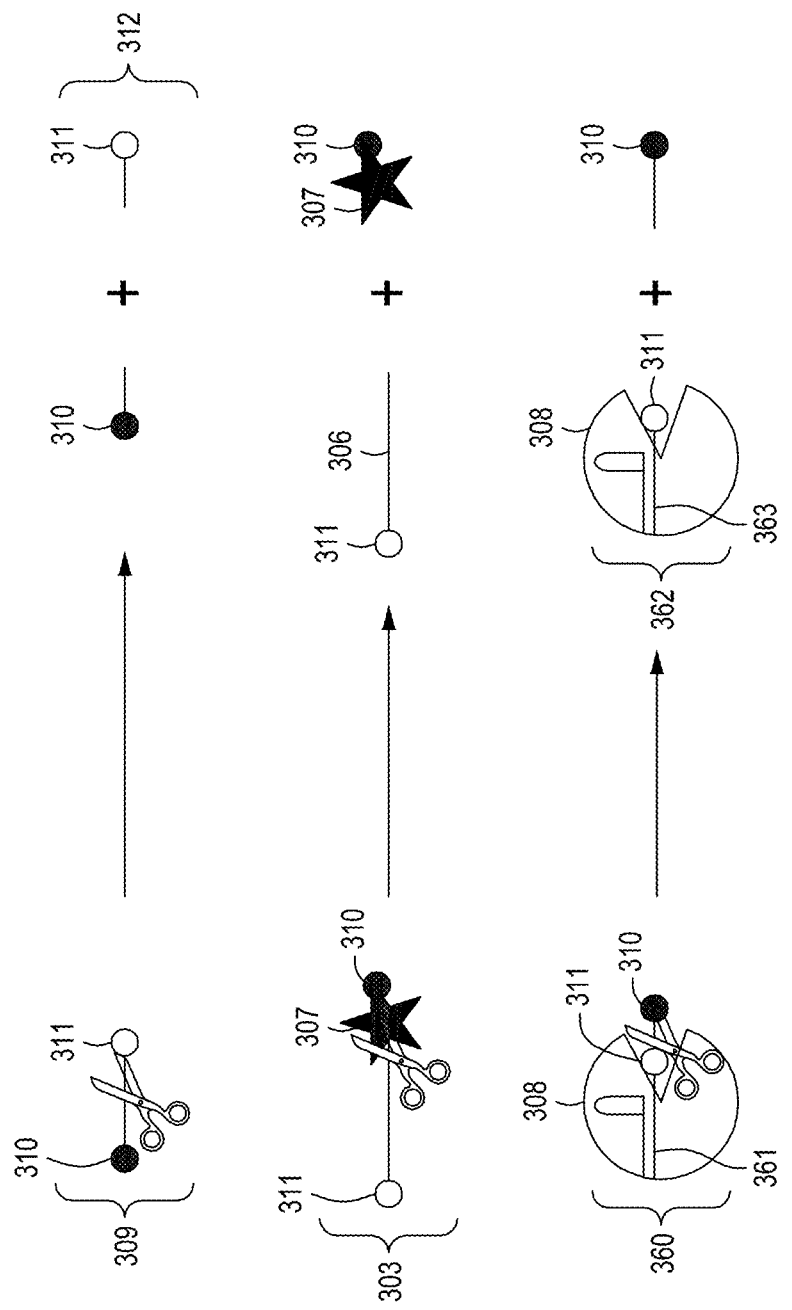
FIG. 3 illustrates three exemplary embodiments of reporter moieties.

As more RNP2s are unquenched (108→110), more trans-cleavage activity is activated and more reporter moieties are unquenched; thus, the binding of the target nucleic acid of interest (104) to RNP1 (102) initiates what becomes a cascade of signal production (120), which increases exponentially; hence, the terms "signal amplification" or "signal boost." The cascade assay thus comprises a single turnover event that triggers a multi-turnover event that then triggers another multi-turnover event in a "cascade." As described below in relation to FIG. 3, the reporter moieties (112) may be provided as molecules that are separate from the other components of the nucleic acid-guided nuclease cascade assay, or the reporter moieties may be covalently or non-covalently linked to the blocked nucleic acid molecules (i.e., the target molecules for the RNP2).

Various components of the sample prep methods, cascade assay, and descriptions of how the cascade assays work are described in detail below.

Target Nucleic Acids of Interest

The target nucleic acids of interest may be a DNA, RNA, or cDNA molecule. Target nucleic acids of interest may be isolated from a sample by standard laboratory techniques. The target nucleic acids of interest originate from source organisms (e.g., cells of source organisms) that are present in a sample, such as a biological sample from a subject (including non-human animals or plants), items of manufacture, or an environmental sample (e.g., water or soil). Non-limiting examples of biological samples include blood, serum, plasma, saliva, mucus, a nasal swab, a buccal swab, a cell, a cell culture, and tissue. The source of the sample could be any mammal, such as, but not limited to, a human, primate, monkey, cat, dog, mouse, pig, cow, horse, sheep, and bat. Samples may also be obtained from any other source, such as air, water, soil, surfaces, food, beverages, nutraceuticals, clinical sites or products, industrial sites (including food processing sites) and products, plants and grains, cosmetics, personal care products, pharmaceuticals, medical devices, agricultural equipment and sites, and commercial samples.

In some embodiments, the target nucleic acids of interest are from one to many infectious agents (e.g., a bacteria, protozoan, insect, worm, virus, or fungus) that affect mammals, including humans. As a non-limiting example, the target nucleic acid of interests could be one or more nucleic acid molecules from bacteria, such as *Bordetella parapertussis, Bordetella pertussis, Chlamydia pneumoniae, Legionella pneumophila, Mycoplasma pneumoniae, Acinetobacter calcoaceticus-baumannii* complex, *Bacteroides fragilis, Enterobacter cloacae* complex, *Escherichia coli, Klebsiella aerogenes, Klebsiella oxytoca, Klebsiella pneumoniae* group, *Moraxella catarrhalis, Proteus* spp., *Salmonella enterica, Serratia marcescens, Haemophilus influenzae, Neisseria meningitidis, Pseudomonas aeruginosa, Stenotrophomonas maltophilia, Enterococcus faecalis, Enterococcus faecium, Listeria monocytogenes, Staphylococcus aureus, Staphylococcus epidermidis, Staphylococcus lugdunensis, Streptococcus agalactiae, Streptococcus pneumoniae, Streptococcus pyogenes, Chlamydia tracomatis, Neisseria gonorrhoeae,* Syphilis (*Treponema pallidum*), *Ureaplasma urealyticum, Mycoplasma genitalium,* and/or *Gardnerella vaginalis.* Also, as a non-limiting example, the target nucleic acid of interest could be one or more nucleic acid molecules from a virus, such as adenovirus, coronavirus HKU1, coronavirus NL63, coronavirus 229E, coronavirus OC43, severe acute respiratory syndrome coronavirus 2 (SARS-COV-2), human metapneumovirus, human rhinovirus, enterovirus, influenza A, influenza A/H1, influenza A/H3, influenza A/H1-2009, influenza B, parainfluenza virus 1, parainfluenza virus 2, parainfluenza virus 3, parainfluenza virus 4, respiratory syncytial virus, herpes simplex virus 1, herpes simplex virus 2, human immunodeficiency virus (HIV), human papillomavirus, hepatitis A virus (HAV), hepatitis B virus (HBV), hepatitis C virus (HCV), and/or human parvovirus B19 (B19V). Also, as a non-limiting example, the target nucleic acid of interest could be one or more nucleic acid molecules from a fungus, such as *Candida albicans, Candida auris, Candida glabrata, Candida krusei, Candida parapsilosis, Candida tropicalis, Cryptococcus neoformans,* and/or *Cryptococcus gattii.* As another non-limiting example, the target nucleic acid of interest could be one or more nucleic acid molecules from a protozoan, such as *Trichomonas vaginalis.*

In some embodiments, other target nucleic acids of interest may be for non-infectious conditions, e.g., to be used for genotyping, including non-invasive prenatal diagnosis of, e.g., trisomies, other chromosomal abnormalities, and known genetic diseases such as Tay Sachs disease and sickle cell anemia. Other target nucleic acids of interest and samples include human biomarkers for cancer. Target nucleic acids of interest may include engineered biologics, including cells such as CAR-T cells, or target nucleic acids of interest from very small or rare samples, where only small volumes are available for testing.

The cascade assays described herein are particularly well-suited for simultaneous testing of multiple to many targets via massively multiplexed gRNAs as described below. Pools of two to 10,000 target nucleic acid molecules of interest may be employed, e.g., pools of two to 1000, two to 100, two to 50, or two to 10 target nucleic acids of interest. As described above, the present disclosure contemplates two to several to many target nucleic acid molecules for loci from each source organism genome (or source chromosome or source cell or source tissue). If RNP1s from different source organisms are contained within the same partition, further testing may be used to identify the specific source organism, if desired.

The methods described herein do not require the target nucleic acids of interest to be DNA, and in fact it is specifically contemplated that the target nucleic acid of interest may be RNA.

Nucleic Acid-Guided Nucleases

The cascade assays comprise nucleic acid-guided nucleases in the reaction mix, either provided as a protein, a coding sequence for the protein, or, in many embodiments, in a ribonucleoprotein (RNP) complex. In some embodiments, the one or more nucleic acid-guided nucleases in the reaction mix may be, for example, a Cas nucleic acid-guided nuclease. Any nucleic acid-guided nuclease having both cis- and trans-cleavage activity may be employed, and the same nucleic acid-guided nuclease may be used for both RNP1 and RNP2 or different nucleic acid-guided nucleases may be used in RNP1 and RNP2. For example, RNP1 and RNP2 may both comprise Cas12a nucleic acid-guided nucleases, or RNP1 may comprise a Cas13 nucleic acid-guided nuclease and RNP2 may comprise a Cas12a nucleic acid-guided nuclease or vice versa. Note that trans-cleavage activity is not triggered unless a target nucleic acid of interest binds to RNP1 or an unblocked nucleic acid molecule binds to RNP2. Nucleic acid-guided nucleases include Type V and Type VI nucleic acid-guided nucleases, as well as nucleic acid-guided nucleases that comprise a RuvC nuclease domain or a RuvC-like nuclease domain but lack an HNH nuclease domain. Nucleic acid-guided nucleases with these properties are reviewed in Makarova and Koonin, Methods Mol. Biol., 1311:47-75 (2015) and Koonin, et al., Current Opinion in Microbiology, 37:67-78 (2020) and updated databases of nucleic acid-guided nucleases and nuclease systems that include newly-discovered systems include BioGRID ORCS (orcs: thebiogrid.org); GenomeCRISPR (genomecrispr.org); Plant Genome Editing Database (plantcrispr.org) and CRISPRCasFinder (crispercas.i2bc.paris-saclay.fr).

The type of nucleic acid-guided nuclease utilized in the method of detection depends on the type of target nucleic acid of interest to be detected. For example, a DNA nucleic acid-guided nuclease (e.g., a Cas12a, Cas14a, or Cas3) should be utilized if the target nucleic acid of interest is a DNA molecule, and an RNA nucleic acid-guided nuclease (e.g., Cas13a or Cas12g) should be utilized if the target nucleic acid of interest is an RNA molecule. Exemplary nucleic acid-guided nucleases include, but are not limited to, Cas RNA-guided DNA nucleic acid-guided nucleases, such as Cas3, Cas12a (e.g., AsCas12a, LbCas12a), Cas12b, Cas12c, Cas12d, Cas12e, Cas14, Cas12h, Cas12i, and Cas12j; Cas RNA-guided RNA nucleic acid-guided nucleases, such as Cas13a (LbaCas13, LbuCas13, LwaCas13), Cas13b (e.g., CccaCas13b, PsmCas13b), and Cas12g; and any other nucleic acid (DNA, RNA, or cDNA) targeting nucleic acid-guided nuclease with cis-cleavage activity and collateral trans-cleavage activity. In some embodiments, the nucleic acid-guided nuclease is a Type V CRISPR-Cas nuclease, such as Cas12a, Cas13a, or Cas14a. In some embodiments, the nucleic acid-guided nuclease is a Type I CRISPR-Cas nuclease, such as Cas3. Type II and Type VI nucleic acid-guided nucleases may also be employed as long as the nucleic acid-guided nuclease exhibits trans-cleavage activity.

In an RNP with a single crRNA (i.e., lacking/without a traceRNA), Cas12a nucleases and related homologs and orthologs interact with a PAM (protospacer adjacent motif) sequence in a target nucleic acid for dsDNA unwinding and R-loop formation. Cas12a nucleases employ a multistep mechanism to ensure accurate recognition of spacer sequences in the target nucleic acid. The WED, REC1 and PAM-interacting (PI) domains of Cas12a nucleases are responsible for PAM recognition and for initiating invasion of the crRNA in the target dsDNA and for R-loop formation.

It has been hypothesized that a conserved lysine residue is inserted into the dsDNA duplex, possibly initiating template strand/non-template strand unwinding. (See Jinek, et al, Mol. Cell, 73 (3): 589-600.e4 (2019).) PAM binding further introduces a kink in the target strand, which further contributes to local strand separation and facilitates base paring of the target strand to the seed segment of the crRNA while the displaced non-target strand is stabilized by interactions with the PAM-interacting domains. (Id.)

The nucleic acid-guided nucleases employed may be wildtype or variants of wildtype Type V nucleases LbCas12a (*Lachnospriaceae bacterium* Cas12a), AsCas 12a (*Acidaminococcus* sp. BV3L6 Cas12a), CtCas12a (*Candidatus Methanoplasma termitum* Cas12a), EcCas12a (*Eubacterium eligens* Cas12a), Mb3Cas12a (*Moraxella bovoculi* Cas12a), FnCas12a (*Francisella novicida* Cas12a), FnoCas12a (*Francisella tularensis* subsp. *novicida* FTG Cas12a), FbCas12a (*Flavobacteriales bacterium* Cas12a), Lb4Cas12a (*Lachnospira eligens* Cas12a), MbCas12a (*Moraxella bovoculi* Cas12a), Pb2Cas12a (*Prevotella bryantii* Cas12a), PgCas12a (*Candidatus Parcubacteria bacterium* Cas12a), AaCas12a (*Acidaminococcus* sp. Cas12a), BoCas12a (*Bacteroidetes bacterium* Cas12a), CMaCas 12a (*Candidatus Methanomethylophilus alvus* CMx1201 Cas12a), and to-be-discovered equivalent Cas12a nucleic acid-guided nucleases and homologs and orthologs of these nucleic acid-guided nucleases (and other nucleic acid-guided nucleases that exhibit both cis-cleavage and trans-cleavage activity.

Guide RNA (gRNA)

The present disclosure detects a target nucleic acid of interest via a reaction mixture containing gRNAs (gRNAs) (i.e., gRNA1s and gRNA2s) incorporated into different RNP complexes (i.e., a variety of different RNP1s and RNP2s). Suitable gRNAs include at least one crRNA region to enable specificity in every reaction. The gRNA Is of the RNP1s are specific to a target nucleic acids of interest and the gRNA2s of the RNP2s are specific to an unblocked nucleic acid (which are described in detail below). As will be clear given the description below, an advantageous feature of the cascade assay is that, with the exception of the gRNA1s in the RNP1s (i.e., the gRNAs specific to the target nucleic acids of interest), the cascade assay components can stay the same (i.e., are identical or substantially identical) no matter what target nucleic acids of interest are being detected, and the gRNA1s in the RNP1s are easily reprogrammable using known techniques and gRNA design tools.

Like the nucleic acid-guided nuclease, the gRNA may be provided in the cascade assay reaction mix in a preassembled RNP, as an RNA molecule, or may also be provided as a DNA sequence to be transcribed, in, e.g., a vector backbone. Providing the gRNA in a pre-assembled RNP complex (i.e., RNP1 or RNP2) is preferred if rapid kinetics are preferred. If provided as a gRNA molecule, the gRNA sequence may include multiple endoribonuclease recognition sites (e.g., Csy4) for multiplex processing. Alternatively, if provided as a DNA sequence to be transcribed, an endoribonuclease recognition site may be encoded between neighboring gRNA sequences such that more than one gRNA can be transcribed in a single expression cassette. Direct repeats can also serve as endoribonuclease recognition sites for multiplex processing. Guide RNAs are generally about 20 nucleotides to about 300 nucleotides in length and may contain a spacer sequence containing a plurality of bases and complementary to a protospacer sequence in the target sequence. The gRNA spacer sequence may be 50%, 60%, 75%, 80%, 85%, 90%, 95%, 97.5%, 98%, 99%, or more complementary to its intended target nucleic acid of interest.

The gRNA of RNP1 is capable of complexing with the nucleic acid-guided nuclease of RNP1 to perform cis-cleavage of a target nucleic acid of interest (e.g., a DNA or RNA), and which triggers non-sequence specific trans-cleavage of other molecules in the reaction mix. Guide RNAs include any polynucleotide sequence having sufficient complementarity with a target nucleic acid of interest (or target sequences generated by unblocking blocked nucleic acid molecules as described below). Target nucleic acids of interest (described above) preferably include a protospacer-adjacent motif (PAM), and, following gRNA binding, the nucleic acid-guided nuclease induces a double-stranded break either inside or outside the protospacer region of the target nucleic acid of interest.

In some embodiments, the gRNA (e.g., of RNP1) is an exo-resistant circular molecule that can include several DNA bases between the 5' end and the 3' end of a natural guide RNA and is capable of binding a target sequence. The length of the circularized guide for RNP1 can be such that the circular form of guide can be complexed with a nucleic acid-guided nuclease to form a modified RNP1 which can still retain its cis-cleavage i.e., (specific) and trans-cleavage (i.e., non-specific) nuclease activity.

In any of the foregoing embodiments, the gRNA may be a modified or non-naturally occurring nucleic acid molecule. In some embodiments, the gRNAs of the disclosure may further contain a locked nucleic acid (LNA), a bridged nucleic acid (BNA), and/or a peptide nucleic acid (PNA). By way of further example, a modified nucleic acid molecule may contain a modified or non-naturally occurring nucleoside, nucleotide, and/or internucleoside linkage, such as a 2'-O-methyl (2'-O-Me) modified nucleoside, a 2'-fluoro (2'-F) modified nucleoside, and a phosphorothioate (PS) bond, or any other nucleic acid molecule modifications described herein.

Ribonucleoprotein (RNP) Complexes

As described above, although the cascade assay "reaction mix" or "reaction mixture" may comprise separate nucleic acid-guided nucleases and gRNAs (or coding sequences therefor), the cascade assays preferably comprise preassembled ribonucleoprotein complexes (RNPs) in the reaction mix, allowing for faster detection kinetics. The present cascade assay employs at least two types of RNP complexes—RNP1 and RNP2—each type containing a nucleic acid-guided nuclease and a gRNA. RNP1 and RNP2 may comprise the same nucleic acid-guided nuclease or may comprise different nucleic acid-guided nucleases; however, the gRNAs in RNP1 and RNP2 are different and are configured to detect different nucleic acids. In some embodiments, the reaction mixture contains about 1 fM to about 10 µM of a given RNP1, or about 1 pM to about 1 µM of a given RNP1, or about 10 pM to about 500 pM of a given RNP1. In some embodiments the reaction mixture contains about $6 \times 10^4$ to about $6 \times 10^{12}$ complexes per microliter (µl) of a given RNP1, or about $6 \times 10^6$ to about $6 \times 10^{10}$ complexes per microliter (µl) of a given RNP1. In some embodiments, the reaction mixture contains about 1 fM to about 500 µM of a given RNP2, or about 1 pM to about 250 µM of a given RNP2, or about 10 pM to about 100 µM of a given RNP2. In some embodiments the reaction mixture contains about $6 \times 10^4$ to about $6 \times 10^{12}$ complexes per microliter (µl) of a given RNP2 or about $6 \times 10^6$ to about $6 \times 10^{12}$ complexes per microliter (µl) of a given RNP2. See Example II below describing preassembling RNPs and Examples V and VI below describing various cascade assay conditions.

In any of the embodiments of the disclosure, the reaction mixture includes 1 to about 1,000 different RNP1s (e.g., 1, 2, 3, 4, 5, 6, 7, 8, 9, 10, 11, 12, 13, 14, 15, 16, 27, 28, 19, 20, 21, 22, 23, 24, 25, 50, 75, 100, 125, 150, 175, 200, 250, 300, 350, 400, 450, 500, 550, 600, 650, 700, 750, 800, 850, 900, 950, 1,0000, or 5,000 or more RNP1s), where different RNP1s comprise a different gRNA polynucleotide sequence. For example, more than one RNP1 may be present for the purpose of targeting one target nucleic acid of interest from many sources or—as is specifically contemplated by the present disclosure—more than one (e.g., several to many) RNP1s will be present for the purpose of targeting more than one target nucleic acid of interest from each source organism (or source chromosome, source cell, source tissue, etc.) in a sample.

In any of the foregoing embodiments and as contemplated herein, the gRNA1 of a specific RNP1 may be homologous or heterologous, relative to the gRNA1 of other RNP1(s) present in the reaction mixture. A homologous mixture of RNP1 gRNAs has a number of gRNAs with the same nucleotide sequence, whereas a heterologous mixture of RNP1 gRNAs has multiple gRNAs with different nucleotide sequences (e.g., gRNAs targeting different loci, genes, variants, and/or microbial species). As contemplated herein, there will be both homologous and heterologous gRNA1s in a given reaction. There will be many RNP1s with the same gRNA1; however, there will be many RNP1s with different gRNA1 sequences. Therefore, the disclosed methods may include a reaction mixture containing more than two heterologous gRNA1s, more than three heterologous gRNA1s, more than four heterologous gRNA1s, more than five heterologous gRNA1s, more than six heterologous gRNA1s, more than seven heterologous gRNA1s, more than eight heterologous gRNA1s, more than nine heterologous gRNA1s, more than ten heterologous gRNAs, more than eleven heterologous gRNA Is, more than twelve heterologous gRNA1s, more than thirteen heterologous gRNA Is, more than fourteen heterologous gRNA1s, more than fifteen heterologous gRNA1s, more than sixteen heterologous gRNA1s, more than seventeen heterologous gRNA1s, more than eighteen heterologous gRNA1s, more than nineteen heterologous gRNA1s, more than twenty heterologous gRNA1s, more than twenty-one heterologous gRNA1s, more than twenty-three heterologous gRNA1s, more than twenty-four heterologous gRNA1s, more than twenty-five heterologous gRNA1s, more than fifty heterologous gRNA1s, more than one hundred heterologous gRNA Is, more than five hundred heterologous gRNA1s, more than one thousand heterologous gRNA1s, or more than five thousand gRNA1s.

As a first non-limiting example of a heterologous mixture of RNP1 gRNAs, the reaction mixture may contain: a number of RNP1s (RNP1-1s) having a gRNA targeting parainfluenza virus 1; a number of RNP1s (RNP1-2s) having a gRNA targeting human metapneumovirus; a number of RNP1s (RNP1-3s) having a gRNA targeting human rhinovirus; a number of RNP1s (RNP1-4s) having a gRNA targeting human enterovirus; and a number of RNP1s (RNP1-5s) having a gRNA targeting coronavirus HKU1. As a second non-limiting example of a heterologous mixture of RNP1 gRNAs, the reaction mixture may contain: a number of RNP1s containing a gRNA targeting two or more SARS-Co-V-2 variants, e.g., B.1.1.7, B.1.351, P.1, B.1.617.2, BA.1, BA.2, BA.2.12.1, BA.4, and BA.5 and subvariants thereof.

As another non-limiting example of a heterologous mixture of RNP1 gRNAs, the reaction mixture may contain RNP1s targeting two or more target nucleic acids of interest from organisms that infect grapevines, such as *Guignardia bidwellii* (RNP1-1), *Uncinula necator* (RNP1-2), *Botrytis cincerea* (RNP1-3), *Plasmopara viticola* (RNP1-4), and *Botryotinis fuckleina* (RNP1-5).

Reporter Moieties

The cascade assay detects a target nucleic acid of interest via detection of a signal generated in the reaction mix by a reporter moiety. In many embodiments the detection of the target nucleic acids of interest occurs within ten minutes including sample prep. Reporter moieties can comprise DNA, RNA, a chimera of DNA and RNA, and can be single stranded, double stranded, or a moiety that is a combination of single stranded portions and double stranded portions.

Depending on the type of reporter moiety used, trans- and/or cis-cleavage by the nucleic acid-guided nuclease in RNP2 releases a signal. In some embodiments, trans-cleavage of stand-alone reporter moieties (e.g., not bound to any blocked nucleic acid molecules) may generate signal changes at rates that are proportional to the cleavage rate, as new RNP2s are activated over time (shown in FIGS. 1C and 2A at bottom, and at top of FIG. 3). Trans-cleavage by either an activated RNP1 or an activated RNP2 may release a signal although the vast majority of trans-cleavage of the reporter moiety is due to the trans-cleavage activity of RNP2. In alternative embodiments and preferably, the reporter moiety may be bound to the blocked nucleic acid molecule, where trans-cleavage of the blocked nucleic acid molecule and conversion to an unblocked nucleic acid molecule may generate signal changes at rates that are proportional to the cleavage rate as new RNP2s are activated over time, thus allowing for real time reporting of results (shown at FIG. 3, center). In yet another embodiment, the reporter moiety may be bound to a blocked nucleic acid molecule such that cis-cleavage following the binding of the RNP2 to an unblocked nucleic acid molecule releases a PAM distal sequence, which in turn generates a signal at rates that are proportional to the cleavage rate (shown at FIG. 3, bottom). In this case, activation of RNP2 by cis-(target specific) cleavage of the unblocked nucleic acid molecule directly produces a signal, rather than producing a signal via indiscriminate trans-cleavage activity. Alternatively or in addition, a reporter moiety may be bound to the gRNA.

The reporter moiety may be a synthetic molecule linked or conjugated to a reporter and quencher such as, for example, a TaqMan probe with a dye label (e.g., FAM or FITC) on the 5' end and a quencher on the 3' end. The reporter and quencher may be about 20-30 bases apart or less (i.e., 10-11 nm apart or less) for effective quenching via fluorescence resonance energy transfer (FRET). Alternatively, signal generation may occur through different mechanisms. Other detectable moieties, labels, or reporters can also be used to detect a target nucleic acid of interest as described herein. Reporter moieties can be labeled in a variety of ways, including direct or indirect attachment of a detectable moiety such as a fluorescent moiety, hapten, or colorimetric moiety.

Examples of detectable moieties include various radioactive moieties, enzymes, prosthetic groups, fluorescent markers, luminescent markers, bioluminescent markers, metal particles, and protein-protein binding pairs, e.g., protein-antibody binding pairs. Examples of fluorescent moieties include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, cyanines, dansyl chloride, phycocyanin, and phycoerythrin. Examples of bioluminescent markers include, but are not limited to, luciferase (e.g., bacterial, firefly, click beetle and the like), luciferin, and acquorin. Examples of enzyme systems having visually detectable signals include, but are not limited to, galactosidases, glucorinidases, phosphatases, peroxidases, and cholinesterases. Identifiable markers also include radioactive elements such as $^{125}$I, $^{35}$S, $^{14}$C, or $^{3}$H. Reporters can also include a change in pH or charge of the cascade assay reaction mix.

The methods used to detect the generated signal will depend on the reporter moiety or moieties used. For example, a radioactive label can be detected using a scintillation counter, photographic film as in autoradiography, or storage phosphor imaging. Fluorescent labels can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Enzymatic labels can be detected by providing the appropriate substrates for the enzyme and detecting the resulting reaction product. Simple colorimetric labels can be detected by observing the color associated with the label. When pairs of fluorophores are used in an assay, fluorophores are chosen that have distinct emission patterns (wavelengths) so that they can be easily distinguished.

Single-stranded, double-stranded or reporter moieties comprising both single- and double-stranded portions can be introduced to show a signal change proportional to the cleavage rate, which increases with every new activated RNP2 complex over time. In some embodiments, reporter moieties can also be embedded into the blocked nucleic acid molecules for real time reporting of results.

For example, the method of detecting a target nucleic acid molecule in a sample using a cascade assay as described herein can involve contacting the reaction mix with a labeled detection ssDNA containing a fluorescent resonance energy transfer (FRET) pair, a quencher/phosphor pair, or both. A FRET pair consists of a donor chromophore and an acceptor chromophore, where the acceptor chromophore may be a quencher molecule. FRET pairs (donor/acceptor) suitable for use include, but are not limited to, EDANS/fluorescein, IAEDANS/fluorescein, fluorescein/tetramethylrhodamine, fluorescein/Cy 5, IEDANS/DABCYL, fluorescein/QSY-7, fluorescein/LC Red 640, fluorescein/Cy 5.5, Texas Red/DABCYL, BODIPY/DABCYL, Lucifer yellow/DABCYL, coumarin/DABCYL, and fluorescein/LC Red 705. In addition, a fluorophore/quantum dot donor/acceptor pair can be used. EDANS is (5-((2-Aminoethyl)amino) naphthalene-1-sulfonic acid); IAEDANS is 5-({2-[(iodoacetyl)amino] ethyl}amino) naphthalene-1-sulfonic acid); DABCYL is 4-(4-dimethylaminophenyl) diazenylbenzoic acid. Useful quenchers include, but are not limited to, BHQ, DABCYL, QSY 7 and QSY 33.

In any of the foregoing embodiments, the reporter moiety may comprise one or more modified nucleic acid molecules, containing a modified nucleoside or nucleotide. In some embodiments the modified nucleoside or nucleotide is chosen from 2'-O-methyl (2'-O-Me) modified nucleoside, a 2'-fluoro (2'-F) modified nucleoside, and a phosphorothioate (PS) bond, or any other nucleic acid molecule modifications described below.

Nucleic Acid Modifications

For any of the nucleic acid molecules described herein (e.g., blocked nucleic acid molecules, gRNAs, and reporter moieties), the nucleic acid molecules may be used in a wholly or partially modified form. Typically, modifications to the blocked nucleic acid molecules, gRNAs, and reporter moieties described herein are introduced to optimize the molecule's biophysical properties (e.g., increasing nucleic acid-guided nuclease resistance and/or increasing thermal stability). Modifications typically are achieved by the incorporation of, for example, one or more alternative nucleosides, alternative sugar moieties, and/or alternative internucleoside linkages.

For example, one or more of the cascade assay components may include one or more of the following nucleoside modifications: 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, and/or 3-deazaguanine and 3-deazaadenine. The nucleic acid molecules described herein (e.g., blocked nucleic acid moleculesgRNAs, reporter molecules) may also include nucleobases in which the purine or pyrimidine base is replaced with other heterocycles, for example 7-deaza-adenine, 7-deazaguanosine, 2-aminopyridine, and/or 2-pyridone. Further modification of the nucleic acid molecules described herein may include nucleobases disclosed in U.S. Pat. No. 3,687,808; Kroschwitz, ed., *The Concise Encyclopedia of Polymer Science and Engineering*, NY, John Wiley & Sons, 1990, pp. 858-859; Englisch, et al., Angewandte Chemie, 30:613 (1991); and Sanghvi, Chapter 16, Antisense Research and Applications, CRC Press, Gait, ed., 1993, pp. 289-302.

In addition to or as an alternative to nucleoside modifications, the cascade assay components may comprise 2' sugar modifications, including 2'-O-methyl (2'-O-Me), 2'-methoxyethoxy (2'-O—CH$_2$CH$_2$OCH$_3$, also known as 2'-O-(2-methoxyethyl) or 2'-MOE), 2'-dimethylaminooxyethoxy, i.e., a O(CH$_2$)$_2$ON(CH$_3$)$_2$ group, also known as 2'-DMAOE, and/or 2'-dimethylaminoethoxyethoxy (also known in the art as 2'-O-dimethylamino-ethoxy-ethyl or 2'-DMAEOE), i.e., 2'-O—CH$_2$OCH$_2$N(CH$_3$)$_2$. Other possible 2'-modifications that can modify the nucleic acid molecules described herein (i.e., blocked nucleic acid molecules, gRNAs, reporter molecules) may include all possible orientations of OH; F; O—, S—, or N-alkyl (mono- or di-); O—, S—, or N-alkenyl (mono- or di-); O—, S- or N-alkynyl (mono- or di-); or O-alkyl-O-alkyl, wherein the alkyl, alkenyl and alkynyl may be substituted or unsubstituted C1 to C10 alkyl or C2 to C10 alkenyl and alkynyl. Other potential sugar substituent groups include, e.g., aminopropoxy (—OCH$_2$CH$_2$CH$_2$NH$_2$), allyl (—CH$_2$—CH═CH$_2$), —O-allyl (—O—CH$_2$—CH═CH$_2$) and fluoro (F). 2'-sugar substituent groups may be in the arabino (up) position or ribo (down) position. In some embodiments, the 2'-arabino modification is 2'-F. Similar modifications may also be made at other positions on the interfering RNA molecule, particularly the 3' position of the sugar on the 3' terminal nucleoside or in 2'-5' linked oligonucleotides and the 5' position of 5' terminal nucleotide. Oligonucleotides may also have sugar mimetics such as cyclobutyl moieties in place of the pentofuranosyl sugar.

Finally, modifications to the cascade assay components may comprise internucleoside modifications such as phosphorothioates, phosphorodithioates, phosphotriesters, aminoalkylphosphotriesters, methyl and other alkyl phosphonates including 3'-alkylene phosphonates, 5'-alkylene phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, and boranophosphates having normal 3'-5' linkages, 2'-5' linked analogs of these, and those having inverted polarity wherein one or more internucleotide linkages is a 3' to 3', 5' to 5' or 2' to 2' linkage.

The Signal Boosting Cascade Assay Employing Blocked Nucleic Acid Molecules

Figure 2A:
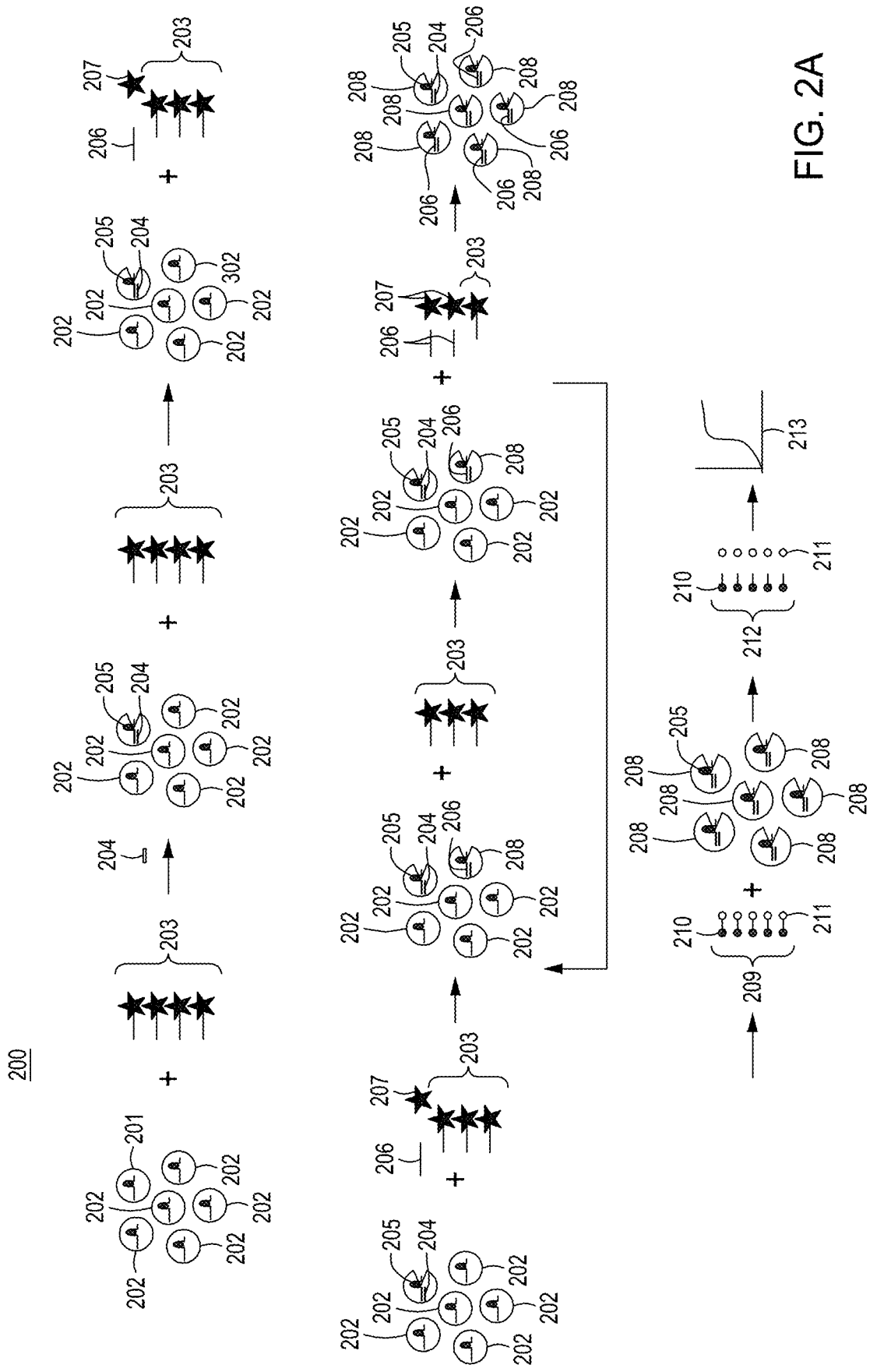
FIG. 2A is a diagram showing the sequence of steps in an exemplary cascade assay utilizing blocked nucleic acid molecules.

As described above, following sample preparation including lysing of the source organisms and splitting of the nucleic acid sample, the cascade assay is performed in partitions comprising specific, known RNP1s. FIG. 1C, described above, depicts the cascade assay generally. A specific embodiment of the cascade assay utilizing blocked nucleic acid molecules is depicted in FIG. 2A and described in detail below. In this embodiment, a blocked nucleic acid is used to prevent the activation of RNP2 in the absence of a target nucleic acid of interest. The method in FIG. 2A begins, at top left, with providing the cascade assay components RNP1 (201), RNP2 (202) and blocked nucleic acid molecules (203). RNP1 (201) (only one is shown) comprises a gRNA specific for a target nucleic acid of interest and a nucleic acid-guided nuclease (e.g., Cas 12a or Cas 14 for a DNA target nucleic acid of interest or a Cas 13a for an RNA target nucleic acid of interest) and RNP2 (202) comprises a gRNA specific for an unblocked nucleic acid molecule and a nucleic acid-guided nuclease (again, e.g., Cas 12a or Cas 14 for a DNA unblocked nucleic acid molecule or a Cas 13a for an RNA unblocked nucleic acid molecule). As described above, the nucleic acid-guided nucleases in RNP1 (201) and RNP2 (202) can be the same or different depending on the type of target nucleic acid of interest and unblocked nucleic acid molecule. What is key, however, is that the nucleic acid-guided nucleases in RNP1 and RNP2 may be activated to have trans-cleavage activity following target nucleic acid or unblocked nucleic acid molecule binding and/or initiation of cis-cleavage activity.

In a first step, a sample—in the present case, an aliquot of a sample—comprising a target nucleic acid of interest (204) is added to the cascade assay reaction mix. Keep in mind that although shown as a single reaction, the method depicted in FIG. 2A is performed in several to many partitions in parallel, where each partition comprises different RNP1s. The target nucleic acid of interest (204) combines with and activates RNP1 (205) but does not interact with or activate RNP2 (202). Once activated, RNP1 binds the target nucleic acid of interest (204) and cuts the target nucleic acid of interest (204) via sequence-specific cis-cleavage, while non-specific trans-cleavage is activated as well, thereby cleaving other nucleic acids present in the reaction mix, including the blocked nucleic acid molecules (203). At least one of the blocked nucleic acid molecules (203) becomes an unblocked nucleic acid molecule (206) when the blocking moiety (207) is removed via cleavage by RNP1. As described below, "blocking moiety" may refer to nucleoside modifications, topographical configurations such as secondary structures, and/or structural modifications.

Once at least one of the blocked nucleic acid molecules (203) is unblocked, the unblocked nucleic acid molecule (206) can then bind to and activate an RNP2 (208). Because the nucleic acid-guided nucleases in the RNP1s (205) and RNP2s (208) have both cis- and trans-cleavage activity, the trans-cleavage activity causes more blocked nucleic acid molecules (203) to become unblocked nucleic acid molecules (206) triggering activation of even more RNP2s (202→208) and more trans-cleavage activity in a cascade. FIG. 2A at bottom depicts the concurrent activation of reporter moieties. Intact reporter moieties (209) comprise a quencher (210) and a fluorophore (211) linked by a nucleic acid sequence. As described above in relation to FIG. 1C, the reporter moieties are also subject to trans-cleavage by activated RNP1 (205) and RNP2 (208). The intact reporter moieties (209) become activated reporter moieties (212) when the quencher (210) is separated from the fluorophore (211), emitting a fluorescent signal (213). Signal strength increases rapidly as more blocked nucleic acid molecules (203) become unblocked nucleic acid molecules (206) triggering cis-cleavage activity of more RNP2s (202→208) and thus more trans-cleavage activity of the reporter moieties (209). Again, the reporter moieties are shown here as separate molecules from the blocked nucleic acid molecules, but other configurations may be employed and are discussed in relation to FIG. 3. One particularly advantageous feature of the cascade assay is that, with the exception of the gRNA in the RNP1 (gRNA1), the cascade assay components are modular in the sense that the components can stay the same no matter what target nucleic acids of interest are being detected.

Figure 2B:
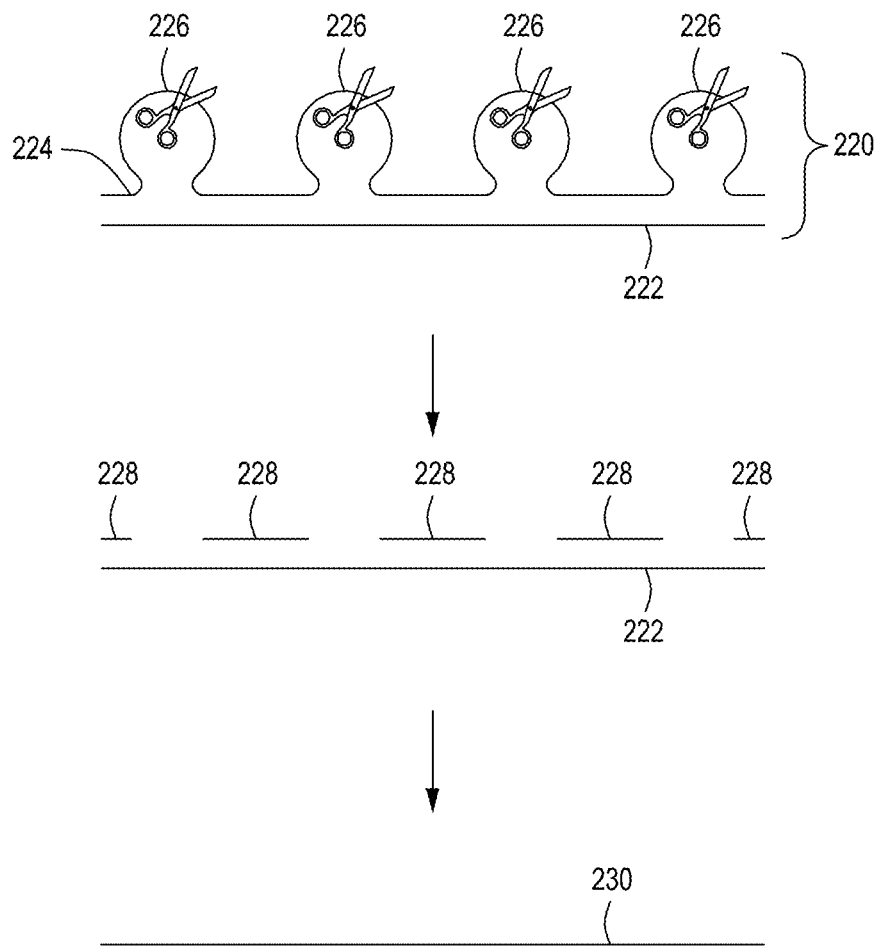
FIG. 2B is a simplified graphic showing an exemplary blocked nucleic acid molecule and a method for unblocking the blocked nucleic acid molecules of the disclosure.

FIG. 2B is a diagram showing an exemplary blocked nucleic acid molecule (220) and an exemplary technique for unblocking the blocked nucleic acid molecules described herein. A blocked single-stranded or double-stranded, circular or linear, DNA or RNA molecule (or a combination of DNA and RNA) (220) comprising a target strand (222) may contain a partial hybridization with a complementary non-target strand nucleic acid molecule (224) containing unhybridized and cleavable secondary loop structures (226) (e.g., hairpin loops, tetraloops, pseudoknots, junctions, kissing hairpins, internal loops, bulges, and multibranch loops). Trans-cleavage of the loops by, e.g., activated RNP1s or RNP2s, generates short strand nucleotide sequences or regions (228) which, because of the short length and low melting temperature $T_m$, can dehybridize at room temperature (e.g., 15°-25° C.), thereby unblocking the blocked nucleic acid molecule (220) to create an unblocked nucleic acid molecule (222→230), enabling the internalization of the unblocked nucleic acid molecule (230) (target strand) into an RNP2, leading to RNP2 activation.

A blocked nucleic acid molecule may be single-stranded or double-stranded, circular or linear, and may further contain a partially hybridized nucleic acid sequence containing cleavable secondary loop structures, as exemplified in FIG. 2B. Such blocked nucleic acid molecules typically have a low binding affinity, or high dissociation constant ($K_d$) in relation to binding to RNP2 and may be referred to herein as a high $K_d$ nucleic acid molecule. In the context of the present disclosure, the binding of blocked or unblocked nucleic acid molecules to RNP2, low $K_d$ values range from about 100 fM to about 1 aM or lower (e.g., 100 zM) and high $K_d$ values are in the range of 100 nM to about 10-100 10 mM and thus are about $10^5$-, $10^6$-, $10^7$-, $10^8$-, $10^9$- to $10^{10}$-fold or higher as compared to low $K_d$ values. Of course, the ideal blocked nucleic acid molecule would have an "infinite $K_d$."

The blocked nucleic acid molecules (high $K_d$ molecules) described herein can be converted into unblocked nucleic acid molecules (low $K_d$ molecules—also in relation to binding to RNP2) via cleavage of nuclease-cleavable regions (e.g., via active RNP1s and RNP2s). The unblocked nucleic acid molecule has a higher binding affinity for the gRNA in RNP2 than does the blocked nucleic acid molecule.

Once the unblocked nucleic acid molecule is bound to RNP2, the RNP2 activation triggers trans-cleavage activity, which in turn leads to more RNP2 activation by further cleaving blocked nucleic acid molecules, resulting in a positive feedback loop or cascade.

In embodiments where blocked nucleic acid molecules are linear and/or form a secondary structure, the blocked nucleic acid molecules may be single-stranded (ss) or double-stranded (ds) and contain a first nucleotide sequence and a second nucleotide sequence. The first nucleotide sequence has sufficient complementarity to hybridize to a gRNA of RNP2, and the second nucleotide sequence does not. The first and second nucleotide sequences of a blocked nucleic acid molecule may be on the same nucleic acid molecule (e.g., for single-strand embodiments) or on separate nucleic acid molecules (e.g., for double-strand embodiments). Trans-cleavage (e.g., via RNP1 or RNP2) of the second nucleotide sequence converts the blocked nucleic acid molecule to a single-strand unblocked nucleic acid molecule. The unblocked nucleic acid molecule contains only the first nucleotide sequence, which has sufficient complementarity to hybridize to the gRNA of RNP2, thereby activating the trans-cleavage activity of RNP2.

In some embodiments, the second nucleotide sequence at least partially hybridizes to the first nucleotide sequence, resulting in a secondary structure containing at least one loop (e.g., hairpin loops, tetraloops, pseudoknots, junctions, kissing hairpins, internal loops, bulges, and multibranch loops). Such loops block the nucleic acid molecule from binding or incorporating into an RNP complex thereby initiating cis- or trans-cleavage.

In some embodiments, the blocked nucleic acid molecule may contain a protospacer adjacent motif (PAM) sequence, or partial PAM sequence, positioned between the first and second nucleotide sequences, where the first sequence is 5' to the PAM sequence, or partial PAM sequence. Inclusion of a PAM sequence may increase the reaction kinetics internalizing the unblocked nucleic acid molecule into RNP2 and thus decrease the time to detection. In other embodiments, the blocked nucleic acid molecule does not contain a PAM sequence.

In some embodiments, the blocked nucleic acid molecules (i.e., high $K_d$ nucleic acid molecules in relation to binding to RNP2) of the disclosure may include a structure represented by Formula I, Formula II, Formula III, or Formula IV as described in detail in U.S. Pat. Nos. 11,693,520; 11,702,686; 11,821,025; 11,820,983; and U.S. Ser. Nos. 17/861,207; 17/861,209; 18/208,272; 18,372,098; 18/078,821; 18/234,402; 18/078,031; 18/204,329 and 18/208,262.

Nucleotide mismatches can be introduced in any of the blocked nucleic acid molecules containing double-strand segments to reduce the melting temperature ($T_m$) of the double-strand segment such that once the loop (L) is cleaved, the double-strand segment is unstable and dehybridizes rapidly. The percentage of nucleotide mismatches of a given segment may vary between 0% and 50%; however, the maximum number of nucleotide mismatches is limited to a number where the secondary loop structure still forms. In other words, the number of hybridized bases can be less than or equal to the length of each double-strand segment and vary based on number of mismatches introduced.

Also, the blocked nucleic acid molecule may be a modified or non-naturally occurring nucleic acid molecule. In some embodiments, the blocked nucleic acid molecules of the disclosure may further contain a locked nucleic acid (LNA), a bridged nucleic acid (BNA), and/or a peptide nucleic acid (PNA). The blocked nucleic acid molecule may contain a modified or non-naturally occurring nucleoside, nucleotide, and/or internucleoside linkage, such as a 2'-O-methyl (2'-O-Me) modified nucleoside, a 2'-fluoro (2'-F) modified nucleoside, and a phosphorothioate (PS) bond, any other nucleic acid molecule modifications described above, and any combination thereof.

In some embodiments, the blocked nucleic acid molecules are circular DNAs, RNAs or chimeric (DNA-RNA) molecules, and the blocked nucleic acid molecules may include different base compositions depending on the Cas enzyme used for RNP1 and RNP2. For the circular design of blocked nucleic acid molecules, the 5' and 3' ends are covalently linked together. This configuration makes internalization of the blocked nucleic acid molecule into RNP2- and subsequent RNP2 activation-sterically unfavorable, thereby blocking the progression of the cascade assay. Thus, RNP2 activation (e.g., trans-cleavage activity) happens after cleavage of a portion of the blocked nucleic acid molecule followed by linearization and internalization of unblocked nucleic acid molecule into RNP2.

In some embodiments, the blocked nucleic acid molecules are topologically circular molecules with 5' and 3' portions hybridized to each other using DNA, RNA, LNA, BNA, or PNA bases which have a very high melting temperature (Tm). The high Tm causes the structure to effectively behave as a circular molecule even though the 5' and 3' ends are not covalently linked. The 5' and 3' ends can also have base non-naturally occurring modifications such as phosphorothioate bonds to provide increased stability.

Reporter Moiety Configurations

FIG. 3 at top depicts the activation of a reporter moiety. Intact reporter moiety (309) comprises a quencher (310) and a fluorophore (311) linked by a nucleic acid sequence. Trans-cleavage by activated RNP1 and RNP2 in the cascade assay separates the quencher (310) from the fluorophore (311), thereby creating an activated reporter moiety (312) that emits a fluorescent signal.

FIG. 3 at center shows a blocked nucleic acid molecule (303), which is also a reporter moiety. In addition to quencher (310) and fluorophore (311), a blocking moiety (307) can be seen (see also blocked nucleic acid molecules 203 in FIG. 2A). Blocked nucleic acid molecule/reporter moiety (353) comprises a quencher (310) and a fluorophore (311). In this embodiment of the cascade assay, when the blocked nucleic acid molecule (303) is unblocked due to trans-cleavage initiated by the target nucleic acid of interest binding to RNP1, the unblocked nucleic acid molecule (306) also becomes an activated reporter moiety with fluorophore (311) separated from quencher (310). Note both the blocking moiety (307) and the quencher (310) are removed. In this embodiment, reporter signal is directly generated as the blocked nucleic acid molecules become unblocked. Embodiments of this schema can be used to supply the bulky modifications to the blocked nucleic acid molecules described below.

FIG. 3 at the bottom shows that cis-cleavage of an unblocked nucleic acid molecule at a PAM distal sequence by RNP2 generates a signal. Shown are activated RNP2

(308), unblocked nucleic acid molecule (361), quencher (310), and fluorophore (311) forming an activated RNP2 with the unblocked nucleic acid/reporter moiety intact (360). Cis-cleavage of the unblocked nucleic acid/reporter moiety (361) results in an activated RNP2 with the reporter moiety activated (362), comprising the activated RNP2 (308), the unblocked nucleic acid molecule with the reporter moiety activated (363), quencher (310) and fluorophore (311). Embodiments of this schema also can be used to supply the bulky modifications to the blocked nucleic acid molecules described below, and in fact a combination of the configurations of reporter moieties shown in FIG. 3 at center and at bottom may be used.

Applications of the Cascade Assay

The present disclosure describes cascade assays for detecting a target nucleic acid of interest in a sample that provide instantaneous or nearly instantaneous results in less than ten minutes including sample prep, allow for massive multiplexing and minimum workflow, and yet provide accurate results at low cost. Moreover, the various embodiments of the cascade assay are notable in that, with the exception of the gRNAs in RNP1, the cascade assay components stay the same no matter what target nucleic acid(s) of interest are being detected, and RNP1 is easily reprogrammed using known guide design tools. As described above, the cascade assay can be massively multiplexed for detecting several to many to target nucleic acid molecules simultaneously without amplification of the nucleic acids in the sample. For example, the assay may be designed to detect several to many different pathogens (e.g., testing for many different pathogens in one assay), or the assay may be designed to detect one to several to many different sequences from the same pathogen (e.g., to increase specificity and sensitivity), or a combination of the two.

As described above, early and accurate identification of, e.g., infectious agents, microbe contamination, and variant nucleic acid sequences that indicate the presence of such diseases such as cancer or contamination by heterologous sources is important in order to select correct therapeutic treatment, identify tainted food, pharmaceuticals, cosmetics and other commercial goods; and to monitor the environment. The cascade assay described herein can be applied in diagnostics for, e.g., infectious disease (including but not limited to Covid, HIV, flu, the common cold, Lyme disease, STDs, chicken pox, diptheria, mononucleosis, hepatitis, UTIs, pneumonia, tetanus, rabies, malaria, dengue fever, Ebola, plague), for rapid liquid biopsies and companion diagnostics (biomarkers for cancers, early detection, progression, monitoring), prenatal testing (including but not limited to chromosomal abnormalities and genetic diseases such as sickle cell, including over-the-counter versions of prenatal testing assays), rare disease testing (achondroplasia, Addison's disease, al-antitrypsin deficiency, multiple sclerosis, muscular dystrophy, cystic fibrosis, blood factor deficiencies), SNP detection/DNA profiling/epigenetics, genotyping, low abundance transcript detection, labeling for cell or droplet sorting, in situ nucleic acid detection, sample prep, library quantification of NGS, screening biologics (including engineered therapeutic cells for genetic integrity and/or contamination), development of agricultural products, food compliance testing and quality control (e.g., detection of genetically modified products, confirmation of source for high value commodities, contamination detection), infectious disease in livestock, infectious disease in cash crops, livestock breeding, drug screening, personal genome testing including clinical trial stratification, personalized medicine, nutrigenomics, drug development and drug therapy efficacy, transplant compatibility and monitoring, environmental testing and forensics, and bioterrorism agent monitoring.

Target nucleic acids of interest are derived from samples as described in more detail above. Suitable samples for testing include, but are not limited to, any environmental sample, such as air, water, soil, surface, food, clinical sites and products, industrial sites and products, pharmaceuticals, medical devices, nutraceuticals, cosmetics, personal care products, agricultural equipment and sites, and commercial samples, and any biological sample obtained from an organism or a part thereof, such as a plant, animal, or microbe. In some embodiments, the biological sample is obtained from an animal subject, such as a human subject. A biological sample may be any solid or fluid sample obtained from, excreted by or secreted by any living organism, including, without limitation, single celled organisms, such as bacteria, yeast, protozoans, and amoebas among others, multicellular organisms including plants or animals, including samples from a healthy or apparently healthy human subject or a human patient affected by a condition or disease to be diagnosed or investigated, such as an infection with a pathogenic microorganism, such as a pathogenic bacteria or virus.

For example, a biological sample can be a biological fluid obtained from a human or non-human (e.g., livestock, pets, wildlife) animal, and may include but is not limited to blood, plasma, serum, urine, stool, sputum, mucous, lymph fluid, synovial fluid, bile, ascites, pleural effusion, seroma, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as rheumatoid arthritis, osteoarthritis, gout or septic arthritis), or a swab of skin or mucosal membrane surface (e.g., a nasal or buccal swab).

The sample can be a viral or bacterial sample or a biological sample that has been minimally processed as described herein, e.g., only treated with a brief lysis step (e.g., sonication or bead beating) prior to detection. In other embodiments, minimal processing can include thermal lysis at an elevated temperature. In some embodiments, minimal processing can include treating the sample with chaotropic salts such as guanidine isothiocyanate or guanidine HCl and in some embodiments, minimal processing may include contacting the sample with reducing agents such as DTT or TCEP and EDTA to inactivate inhibitors and/or other nucleases present in the samples. In other embodiments, minimal processing for biofluids may include centrifuging the samples to obtain cell-debris free supernatant before applying the reagents.

The components of the cascade assay may be provided in various kits for testing at, e.g., point of care facilities, in the field, pandemic testing sites, and the like. In one aspect, the kit for detecting target nucleic acids of interest in a sample includes: several to many to massively multiplexed first ribonucleoprotein complexes (RNP1s) (separated into partitions), second ribonucleoprotein complexes (RNP2s), blocked nucleic acid molecules, and reporter moieties. The first complexes (RNP1s) comprise a first nucleic acid-guided nuclease and the first gRNAs (gRNA1s) (again, separated into partitions), where the first gRNAs include the sequence complementary to the target nucleic acids of interest.

Any of the kits described herein may further include a sample collection device, e.g., a syringe, lancet, nasal swab, or buccal swab for collecting a biological sample from a subject, and/or a sample preparation reagent, e.g., a lysis reagent. The kits can be used with an instrument comprising a sample prep module and a detection module). Each component of the kit may be in a separate container or two or more components may be in the same container although the RNP1s will be partitioned. In addition, the kit may further include instructions for use and other information.

EXAMPLES

The following examples are put forth so as to provide those of ordinary skill in the art with a complete disclosure and description of how to make and use the present invention and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Preparation of Sample Nucleic Acids

The workflows described herein contemplate collecting samples via nasal or nasopharyngeal swabs and detecting viruses and/or gram negative and/or gram positive bacteria source organisms. Further, the workflows worked with small sample volumes in an automated instrument comprising two modules: a sample prep module and a detection module, with detection of source organisms achieved within 10 minutes including time for sample prep.

Note that the volumes recited in this Example I are exemplary and may be doubled, halved, or increased or decreased by X % depending on the type of swab used for collection and the source of the sample. The aim is to minimize the extraction volume yet maximize extraction efficiency. For the purposes of this Example, it was estimated that 800 copies of each source organism genome are introduced via the swab; however, the swab absorbs a portion of the extraction buffer. In a next step—with the assumption the swab absorbs <~50% of the extraction buffer—a 100 µL aliquot of the sample was subjected to a bead beating procedure at 95° C. Bead-beating can be performed at 25-95° C., but 95° C. is used to inactivate nucleases released from the lysed cells. The 50% reduction in volume also decreases the estimated number copies of each source organism genome to, e.g., 400 copies.

In the present protocols, 100 µm glass or zirconia-silicate beads (BioSpec, Bartelsville, OK USA) were used and a custom bead beater instrument was utilized. Alternatively, commercially available bead beating systems are known and include the Biospec BeadBeater, Powerlyzer 24 Homogenizer, the Fisherbrand™ Bead Mill, the Bead Bug™ microtube homogenizer, and the suite of MP FastPrep™ Instruments. In the present Example, the bead beating system that was used was configured for 100 µL samples where the volume is minimized for quick lysis and nucleic acid fragmentation. In this first workflow, a temperature of 95° C. in the presence at 100 mM TCEP and 1 mM EDTA was used to inactivate RNases present in the sample. Following the bead beating step, the sample was diluted with 400 µL of the reaction mixture comprising the RNP2s and blocked nucleic acid molecules (for example, see step (16) in FIG. 1A) in buffer, thereby reducing the concentration of any potential inhibitors of the cascade reaction by 5-fold. After dilution, the sample was split into 20 µL aliquots distributed into, e.g., 25 µL partitions, where the partitions comprised known first ribonucleoprotein complexes (RNP1s) comprising the first nucleic acid-guided nuclease and first gRNA1s. As described above, there may be a total of tens to hundreds of different first gRNAs (gRNA1s) represented in RNP1s and distributed into the partitions; such as gRNA1s targeting ten or more different loci in, e.g., one source organism or gRNA1s targeting ten or more different loci in two, three, four or more source organisms depending on the breadth of the cascade assay. The RNP1s in the partitions may be in solution, or may be lyophilized, or attached to a bead carrier. Once the sample/reaction mixture is distributed into the wells containing the different RNP1s, the cascade assay is initiated if one or more target nucleic acid molecules are present in the sample and, e.g., fluorescent signals in the partitions are detected.

A second exemplary workflow for sample preparation and sample splitting comprises the use of EDTA (ethylenediaminetetraacetic acid), a divalent chelator, reducing agents such as TCEP (Tris(2-carboxyethyl) phosphine hydrochloride or DTT (dithiothreitol), and employing heating to 95° C. to inactivate nucleases. In a first step, the collection swab was extracted in, e.g., 200 µL of a buffer comprising EDTA and either TCEP or DTT. Again, the aim was to minimize the extraction volume yet maximize extraction efficiency and it was estimated that ~800 copies of each source organism genome resulted from the extraction. In a next step, 100 µL of the sample was subjected to a bead beating procedure.

In this second workflow, 100 µm glass or zirconia-silicate beads (BioSpec, Bartelsville, OK USA) were used and a custom bead beater instrument was utilized and the bead beating system used was configured for 100 µL samples. Following the bead beating step, the sample was diluted with 400 µL of the reaction mixture comprising the RNP2s and blocked nucleic acid molecules (again see step (16) in FIG. 1A) in buffer. After dilution, however, in this workflow the sample was not split into aliquots. Instead, the first ribonucleoprotein complexes (RNP1s) were spotted onto an array with interstitial regions separating the spots. The sample/reaction mixture was delivered in bulk to the array containing the RNP1s. The cascade assay is initiated if target nucleic acid molecules are present in the sample and, e.g., fluorescent signals in the partitions are detected.

A third exemplary workflow for sample preparation and sample splitting comprises the use of guanidinium thiocyanate (GuSCN) at a temperature of 25° C. In a first step, the collection swab was extracted in 400 µL in a buffer comprising GuSCN. Other guanidinium extraction chemistries such as guanidinium hydrochloride (GuHCl), and guanidinium isothiocyanate (GITC) could be used. Again, the aim was to minimize the extraction volume yet maximize extraction efficiency and it is estimated that 800 copies of each source organism genome will result from the extraction. In a next step, 300 µL of the sample was subjected to a bead beating procedure at 25° C., where the number of copies of the genome for each source organism genome is decreased to approximately 600 copies. For this protocol, nucleic acids were induced to bind to the beads via the GuSCN binding buffer, the beads were washed with a low salt solution to remove unbound material, and the nucleic acids were eluted from the beads in 300 µL elution solution (water, Tris HCl, or NaOH) at 70° C.-95° C. The conventional ethanol wash after the binding step, and then drying of the beads with bound nucleic acids was not performed; instead, the ethanol wash and air dry was replaced with washing in the beads with a low salt solution and no drying step was performed. Results of this process resulted in ~50% DNA recovery (data not shown). Since nucleic acid purification recoveries are ~50%, the number of copies of the genome for each source organism is decreased to approximately 300 copies. Nucleic acid fragmentation or additional nucleic acid fragmentation can be accomplished at the elution step since DNA in a no-salt solution will fragment at high temperature and RNA in a high alkalinity solution will fragment at high temperature.

Again, 100 μm glass or zirconia-silicate beads (BioSpec, Bartlesville, OK USA) were used and a custom bead beater instrument was utilized and the bead beating system used was configured for 300 μL samples where the volume is minimized for quick lysis. Again note that no ethanol washing or drying steps were required. Following the bead beating and binding, washing, and elution at a temperature of 70-95° C., the sample was mixed with 200 μL of the reaction mixture comprising the RNP2s and blocked nucleic acid molecules (for example, see step (16) in FIG. 1A) in buffer. After mixing, the sample is split into 20 aliquots distributed into, e.g., 25 μL partitions, where the partitions comprise known first ribonucleoprotein complexes (RNP1s) where the RNP1s comprise a first nucleic acid-guided nuclease and first gRNAs (gRNA1s). As described above, there may be a total of tens to hundreds to thousands of different gRNA Is represented in RNP1s and distributed into partitions; such as gRNA1s targeting ten or more different loci in, e.g., one source organism or gRNA Is targeting ten or more different loci in two, three, four or more source organisms depending on the breadth of the cascade assay. Once the sample/reaction mixture is distributed into the wells containing the RNP1s, the cascade assay is initiated if one or more target nucleic acid molecules are present in the sample and, e.g., fluorescent signals in the partitions are detected.

A fourth exemplary workflow for sample preparation and sample splitting comprises guanidinium thiocyanate (GuSCN) at a temperature of 25° C. In a first step, the collection swab was extracted in 200 μL of a buffer comprising GuSCN. Again, the aim was to minimize the extraction volume yet maximize extraction efficiency and it was estimated that ~800 copies of each source organism genome resulted from the extraction. In a next step, 100 μL of the sample was subjected to a bead beating procedure at 25° C., however in this example it was assumed that the number of copies of each source organism genome will be decreased to 200 copies. Again note that in the present protocol, the typical nucleic acid purification protocol of binding the nucleic acids, performing an ethanol wash, then drying the nucleic acids was not used; instead, the ethanol wash and air dry was replaced with washing in low salt with no drying step. Results of this process resulted in ~50% DNA recovery (data not shown).

In the present protocols, 100 μm glass or zirconia-silicate beads (BioSpec, Bartlesville, OK USA) were used, a custom bead beater instrument was utilized and the bead beating system used was configured for 100 μL samples. Following the bead elution step at a temperature of 70-95° C., the sample was mixed with 100 μL of the reaction mixture comprising the RNP2s and blocked nucleic acid molecules (again see step (16) in FIG. 1A) in buffer. After mixing, however, in this fourth workflow, like the second workflow, the sample is not split into aliquots. Instead, the first ribonucleoprotein complexes (RNP1s) are spotted onto an array with interstitial regions separating the spots, and the sample/reaction mixture is delivered in bulk to the array containing the RNP1s. The cascade assay is initiated if target nucleic acid molecules are present in the sample and, e.g., fluorescent signals in the partitions are detected.

Example II: RNP Formation

For RNP complex formation, 250 nM of LbCas12a nuclease protein was incubated with 375 nM of a target specific gRNA in 1× Buffer (10 mM Tris-HCl, 100 μg/mL BSA) with 2-15 mM MgCl$_2$ at 25° C. for 20 minutes. The total reaction volume was 2 μL. Other ratios of LbCas12a nuclease to gRNAs were tested, including 1:1, 1:2 and 1:5. The incubation temperature ranged from 16° C.-37° C., and the incubation time ranged from 10 minutes to 4 hours.

Example III: Blocked Nucleic Acid Molecule Formation

Ramp cooling: For formation of the secondary structure of blocked nucleic acid molecules, 2.5 μM of a blocked nucleic acid molecule was mixed in a T50 buffer (20 mM Tris HCl, 50 mM NaCl) with 10 mM MgCl$_2$ for a total volume of 50 μL. The reaction was heated to 95° C. at 1.6° C./second and incubated at 95° C. for 5 minutes to dehybridize any secondary structures. Thereafter, the reaction was cooled to 37° C. at 0.015° C./second to form the desired secondary structure.

Snap cooling: For formation of the secondary structure of blocked nucleic acid molecules, 2.5 μM of a blocked nucleic acid molecule was mixed in a T50 buffer (20 mM Tris HCl, 50 mM NaCl) with 10 mM MgCl$_2$ for a total volume of 50 μL. The reaction was heated to 95° C. at 1.6° C./second and incubated at 95° C. for 5 minutes to dehybridize any secondary structures. Thereafter, the reaction was cooled to room temperature by removing the heat source to form the desired secondary structure.

Snap cooling on ice: For formation of the secondary structure of blocked nucleic acid molecules, 2.5 M of a blocked nucleic acid molecule was mixed in a T50 buffer (20 mM Tris HCl, 50 mM NaCl) with 10 mM MgCl$_2$ for a total volume of 50 μL. The reaction was heated to 95° C. at 1.6° C./second and incubated at 95° C. for 5 minutes to dehybridize any secondary structures. Thereafter, the reaction was cooled to room temperature by placing the reaction tube on ice to form the desired secondary structure.

Example IV: Reporter Moiety Formation

The reporter moieties used in the reactions herein were single-stranded DNA oligonucleotides 5-9 bases in length (e.g., with sequences of TTATT, TTTATTT, ATTAT, ATTTATTTA, AAAAA, or AAAAAAAAA) with a fluorophore and a quencher attached on the 5' and 3' ends, respectively. In one example using a Cas12a cascade, the fluorophore was FAM-6 and the quencher was IOWA BLACK® (Integrated DNA Technologies, Coralville, IA). In another example using a Cas13 cascade, the reporter moieties were single-stranded RNA oligonucleotides 5-10 bases in length (e.g., r(U)n, r(UUAUU)n, r(A)n).

Example V: Cascade Assay

Format I (final reaction mix components added at the same time): RNP1 was assembled using the LbCas12a nuclease and a gRNA for the Methicillin resistant *Staphylococcus aureus* (MRSA) DNA according to the RNP complex formation protocol described in Example II. Briefly, 250 nM LbCas12a nuclease was assembled with 375 nM of the MRSA-target specific gRNA. Next, RNP2 was formed using the LbCas12a nuclease and a gRNA specific for a selected blocked nucleic acid molecule using 500 nM LbCas12a nuclease assembled with 750 nM of the blocked nucleic acid-specific gRNA incubated in 1×NEB 2.1 Buffer (New England Biolabs, Ipswich, MA) with 5 mM $MgCl_2$ at 25° C. for 20-40 minutes. Following incubation, RNP1s were diluted to a concentration of 75 nM LbCas12a: 112.5 nM gRNA. Thereafter, the final reaction was carried out in 1× Buffer, with 500 nM of the ssDNA reporter moiety, 1×ROX dye (Thermo Fisher Scientific, Waltham, MA) for passive reference, 2.5 mM $MgCl_2$, 4 mM NaCl, 15 nM LbCas12a: 22.5 nM gRNA RNP1, 20 nM LbCas12a: 35 nM gRNA RNP2, and 50 nM blocked nucleic acid molecule in a total volume of 9 µL. 1 µL of MRSA DNA target was added to make a final volume of 10 µL. The final reaction was incubated in a thermocycler at 25° C. with fluorescence measurements taken every 1 minute.

Format II (RNP1 and MRSA target pre-incubated before addition to final reaction mix): RNP1 was assembled using the LbCas12a nuclease and a gRNA for the MRSA DNA according to the RNP formation protocol described in Example II. Briefly, 250 nM LbCas12a nuclease was assembled with 375 nM of the MRSA-target specific gRNA. Next, RNP2 was formed using the LbCas12a nuclease and a gRNA specific for a selected blocked nucleic acid molecule using 500 nM LbCas12a nuclease assembled with 750 nM of the blocked nucleic acid-specific gRNA incubated in 1×NEB 2.1 Buffer (New England Biolabs, Ipswich, MA) with 5 mM $MgCl_2$ at 25° C. for 20-40 minutes. Following incubation, RNP1s were diluted to a concentration of 75 nM LbCas12a: 112.5 nM gRNA. After dilution, the formed RNP1 was mixed with 1 µL of MRSA DNA target and incubated at 16° C.-37° C. for up to 10 minutes to activate RNP1. The final reaction was carried out in 1× Buffer, with 500 nM of the ssDNA reporter moiety, 1×ROX dye (Thermo Fisher Scientific, Waltham, MA) for passive reference, 2.5 mM $MgCl_2$, 4 mM NaCl, the pre-incubated and activated RNP1, 20 nM LbCas12a: 35 nM gRNA RNP2, and 50 nM blocked nucleic acid molecule in a total volume of 9 µL. The final reaction was incubated in a thermocycler at 25° C. with fluorescence measurements taken every 1 minute.

Format III (RNP1 and MRSA target pre-incubated before addition to final reaction mix and blocked nucleic acid molecule added to final reaction mix last): RNP1 was assembled using the LbCas12a nuclease and a gRNA for the MRSA DNA according to the RNP complex formation protocol described in Example II. Briefly, 250 nM LbCas12a nuclease was assembled with 375 nM of the MRSA-target specific gRNA. Next, RNP2 was formed using the LbCas12a nuclease and a gRNA specific for a selected blocked nucleic acid molecule using 500 nM LbCas12a nuclease assembled with 750 nM of the blocked nucleic acid-specific gRNA incubated in 1×NEB 2.1 Buffer (New England Biolabs, Ipswich, MA) with 5 mM $MgCl_2$ at 25° C. for 20-40 minutes. Following incubation, RNP1s were diluted to a concentration of 75 nM LbCas12a: 112.5 nM gRNA. After dilution, the formed RNP1 was mixed with 1 µL of MRSA DNA target and incubated at 16° C.-37° C. for up to 10 minutes to activate RNP1. The final reaction was carried out in 1× Buffer, with 500 nM of the ssDNA reporter moiety, 1×ROX dye (Thermo Fisher Scientific, Waltham, MA) for passive reference, 2.5 mM $MgCl_2$, 4 mM NaCl, the pre-incubated and activated RNP1, and 20 nM LbCas12a: 35 nM gRNA RNP2 in a total volume of 9 µL. Once the reaction mix was made, 1 µL (50 nM) blocked nucleic acid molecule was added for a total volume of 10 µL. The final reaction was incubated in a thermocycler at 25° C. with fluorescence measurements taken every 1 minute.

Example VI: Detection of MRSA and Test Reaction Conditions

To detect the presence of Methicillin resistant *Staphylococcus aureus* (MRSA) and determine the sensitivity of detection with the cascade assay, titration experiments with a MRSA DNA target nucleic acid of interest were performed. The MRSA DNA sequence was derived from NCBI Reference Sequence NC: 007793.1.

Briefly, an RNP1 was preassembled with a gRNA sequence designed to target MRSA DNA. Specifically, RNP1 was designed to target a 20 bp region of the mecA gene of MRSA. An RNP2 was preassembled with a gRNA sequence designed to target the unblocked nucleic acid molecule that results from unblocking (i.e., linearizing) blocked nucleic acid molecule. The reaction mix contained the preassembled RNP1, preassembled RNP2, and a blocked nucleic acid molecule, in a buffer (pH of about 8) containing 4 mM $MgCl_2$ and 101 mM NaCl.

The blocked nucleic acid molecule used herein had a secondary structure free energy value of −5.84 kcal/mol and relatively short self-hybridizing, double-stranded regions of 5 bases and 6 bases. Results were achieved for detection of 3E4 copies, 30 copies, 3 copies and 0 copies of the mecA gene of MRSA (n=3) at 25° C. with varying concentrations of blocked nucleic acid, RNP2 and reporter moiety. When 100 nM blocked nucleic acid molecules, 10 nM RNP2s and 500 nM reporter moieties are used, the ratio of blocked nucleic acid molecules to RNP2s was 10:1. With 3E4 copies, nearly 100% of the reporters were cleaved at t=0 with a signal-to-noise ratio of 28.06 at 0 minutes, a signal-to-noise ratio of 24.23 at 5 minutes, and a signal-to-noise ratio of 21.01 at 10 minutes (data not shown). Additionally, the signal-to-noise ratios for detection with 30 copies of MRSA target was 12.45 at 0 minutes, 14.07 at 5 minutes and 16.16 at 10 minutes; and the signal-to-noise ratios for detection with 3 copies of MRSA target is 1.79 at 0 minutes, 1.64 at 5 minutes and is 2.04 at 10 minutes. Note the measured fluorescence at 0 copies increases only slightly over the 10- and 30-minutes intervals, resulting in a flat negative. A flat negative (the results obtained over the time period for 0 copies) demonstrated that there is very little non-specific or undesired signal generation in the system.

While certain embodiments have been described, these embodiments have been presented by way of example only and are not intended to limit the scope of the present disclosures. Indeed, the novel methods, apparatuses, modules, instruments and systems described herein can be embodied in a variety of other forms; furthermore, various omissions, substitutions and changes in the form of the methods, apparatuses, modules, instruments and systems described herein can be made without departing from the spirit of the present disclosures. The accompanying claims and their equivalents are intended to cover such forms or modifications as would fall within the scope and spirit of the present disclosures.

I claim:
1. A method for identifying one or more target nucleic acids of interest from two or more source organisms in a sample comprising the steps of:
   obtaining a sample;
   lysing the source organisms and fractionating nucleic acids obtained from the lysed source organisms in the sample, wherein the nucleic acids are fractionated into lengths of 50 bp to 100,000 bp;

designing a plurality of first guide nucleic acids (gRNA1s) complementary to a plurality of loci in each genome of the two or more source organisms;

forming first ribonucleoprotein complexes (RNP1s) comprising a first nucleic acid-guided nuclease and the gRNA1s; wherein the first nucleic acid-guided nuclease exhibits both cis- and trans-cleavage activity and wherein the RNP1s are formed in partitions where different partitions comprise different gRNA1 sequences;

providing a reaction mixture comprising:
second ribonucleoprotein complexes (RNP2s) comprising a second nucleic acid-guided nuclease and a second gRNA that is not complementary to the target nucleic acids of interest; wherein the second nucleic acid-guided nuclease exhibits both cis- and trans-cleavage activity; and
a plurality of blocked nucleic acid molecules comprising a sequence corresponding to the second gRNA, wherein a $K_d$ of the blocked nucleic acid molecules binding to the RNP2s is from 100 nM to 100 µM;

contacting the RNP1s in each partition with the reaction mixture and the fractionated nucleic acids in the sample under conditions that allow the target nucleic acids of interest in the sample to bind to RNP1, wherein upon binding of target nucleic acids of interest the RNP1s become active initiating trans-cleavage of at least one of the plurality of blocked nucleic acid molecules thereby producing at least one unblocked nucleic acid molecule, wherein a $K_d$ of the at least one unblocked nucleic acid molecule binding to the RNP2 is from 100 fM to 1 aM and wherein the at least one unblocked nucleic acid molecule binds to RNP2 initiating trans-cleavage of at least one further blocked nucleic acid molecule; and detecting cleavage products from each partition, thereby detecting the target nucleic acids of interest in the sample.

2. The method of claim 1, wherein one or both of RNP1 and RNP2 comprise a nucleic acid-guided nuclease selected from Cas3, Cas12a, Cas12b, Cas12c, Cas12d, Cas12e, Cas14, Cas12h, Cas12i, Cas12j, Cas13a, or Cas13b.

3. The method of claim 1, wherein the reaction mixture further comprises a reporter moiety.

4. The method of claim 3, wherein the reporter moiety comprises a fluorescent, chemiluminescent, radioactive, colorimetric or other optical signal.

5. The method of claim 4, wherein the reporter moiety comprises the fluorescent signal.

6. The method of claim 4, wherein the reporter moiety comprises the chemiluminescent signal.

7. The method of claim 4, wherein the reporter moiety comprises the colorimetric signal.

8. The method of claim 3 wherein the reporter moiety is not operably linked to the blocked nucleic acid molecules.

9. The method of claim 3, wherein the reporter moiety is operably linked to the blocked nucleic acid molecules.

10. The method of claim 1, wherein the lysing step is performed at 95° C.

11. The method of claim 1, wherein the lysing step is performed using bead beating.

12. The method of claim 1, wherein the lysing step is performed using sonication.

13. The method of claim 1, wherein the lysing step is performed using a lysing buffer comprising EDTA.

14. The method of claim 1, wherein the lysing step is performed using a lysing buffer comprising TCEP.

15. The method of claim 1, wherein the lysing step is performed using a lysing buffer comprising DTT.

16. The method of claim 1, wherein the lysing step is performed using a lysing buffer comprising isothiocyanate.

17. The method of claim 1, further comprising a nucleic acid purification step after the lysing step.

18. The method of claim 1, wherein the partitions are wells.

19. The method of claim 1, wherein the partitions are spots separated by interstitial regions.

20. The method of claim 1, wherein the partitions are droplets.

21. The method of claim 1, wherein the nucleic acids are fractionated into lengths of 50 bp to 5,000 bp.

22. The method of claim 21, wherein the nucleic acids are fractionated into lengths of 100 bp to 1,000 bp.

23. The method of claim 22, wherein the nucleic acids are fractionated into lengths of 100 bp to 500 bp.

24. The method of claim 1, wherein the nucleic acids are fractionated into lengths of 30 bp to 500 bp.

25. The method of claim 24, wherein the nucleic acids are fractionated into lengths of 30 bp to 100 bp.

26. The method of claim 1, wherein at least three gRNA1s complementary to loci in each genome of each source organism are designed.

27. The method of claim 26, wherein at least four gRNA1s complementary to loci in each genome of each source organism are designed.

28. The method of claim 27, wherein at least five gRNA1s complementary to loci in each genome of each source organism are designed.

29. The method of claim 28, wherein at least ten gRNA1s complementary to loci in each genome of each source organism are designed.

30. The method of claim 29, wherein at least twenty gRNA1s complementary to loci in each genome of each source organism are designed.

* * * * *